(12) United States Patent
Mercep et al.

(10) Patent No.: US 6,897,211 B2
(45) Date of Patent: May 24, 2005

(54) THIENODIBENZOAZULENE COMPOUNDS AS TUMOR NECROSIS FACTOR INHIBITORS

(75) Inventors: Mladen Mercep, Zagreb (HR); Milan Mesic, Zagreb (HR); Dijana Pesic, Sibanik (HR); Zeljko Zupanovic, Zagreb (HR); Boska Hrvacic, Velika Gorica (HR)

(73) Assignee: Pliva-Istrazivacki Institut d.o.o., Zagreb (HR)

(*) Notice: Subject to any disclaimer, the term of this patent is extended or adjusted under 35 U.S.C. 154(b) by 0 days.

(21) Appl. No.: 10/298,217

(22) Filed: Nov. 18, 2002

(65) Prior Publication Data

US 2003/0153750 A1 Aug. 14, 2003

Related U.S. Application Data

(63) Continuation-in-part of application No. PCT/HR01/00027, filed on May 16, 2001.

(30) Foreign Application Priority Data

May 17, 2000 (HR) ..................................... P 20000310 A

(51) Int. Cl.$^7$ ...................... C07D 495/04; A61K 31/55; A61P 35/00
(52) U.S. Cl. ..................... 514/215; 514/232.8; 514/321; 514/422; 514/439; 514/440; 540/576; 544/146; 546/202; 548/525; 549/42
(58) Field of Search .............................. 514/215, 232.8, 514/321, 422, 439, 440; 540/576; 544/146; 546/202; 548/525; 549/42

(56) References Cited

PUBLICATIONS

Postmarketing Adverse Event Data for TNF–alpha Antagonists (Oct. 23, 2001) Stephen A. Paget, MD <http://rheumatology.hss.edu/phys/specialreports/pagettnf.asp>.*
Green (Using TNF alpha technology to treat rheumatoid arthrits) Article (Jul./Aug. 2004) <http://rheumatology.hss.edu/phys/specialreports/pagettnf.asp>.*
Centocor products (Aug. 11, 2004 <http://www.centocor.com/cgi–bin/site/products/prod_remicade.cgi is cited for the statement that>.*
"News & Notices" http://www.psoriasis.org/enbrel.approval.jan02.htm (Jul. 30, 2002).*
Cagniat et al. (Comptes. Rendus des Seances de I'Academie des Sciences, Serie C: Sciences Chimiques (1976). Abstract.*
Aderka, D., Isr. J. Med. Sci., 1991, 27:52–60; "Role of tumor necrosis factor in the pathogenesis of intravascular coagulopathy of sepsis: potential new therapeutic implications."
Heilig, B. et al., Clinical Investigation 1992: 70:22–27 "Elevated TNF Receptor Plasma Concentrations in Patients with Rheumatoid Arthritis".
Tomizawa S. et al., Nephron. 1993, 63: 111–112; "TNF inhibitory activity in the urine of chronic renal failure patients with glomerulonephritis."
Egido J. et al., Kidney Int. Suppl. 1993, 39:59–64; "Role of tumor necrosis factor–alpha in the pathogenesis of glumerular diseases."
Piguet P.F. et al., Am. J. Pathol. 1993, 143:651–655; "Expression and localization of tumor necrosis factor–alpha and its mRNA in idiopathic pulmonary fibrosis."
Gauldie J. et al., Thorax, 1993, 48:931–935; "Cytokines and pulmonary fibrosis."
Badger A.M. et al. Circ. Shock 1994 44(4):188–195; "Beneficial effects of the phosphodiesterase inhibitors BRL 61063, pentoxifylline, and rolipram in a murine model of endotoxin shock."
Di Francia M. et al. AM. J. Respir. Crit. Care Med. 1994, 150:1453–1455; "Tumor necrosis factor–alpha levels and weight loss in chronic obstructive pulmonary disease."
Hotamisligil G.S., Spiegelman B.M., Diabetes, 1994, 43:1271–1278; "Tumor necrosis factor alpha: a key component of the obesity–diabetes link."
Piguet P.F., Vesin C., Eur. respire. J., 1994, 7:515–518; "Treatment by human recombinant soluble TNF receptor of pulmonary fibrosis induced by bleomycin or silica in mice."
Bissonnette E. Y. et al., Clin. Exp. Immunol. 1995, 102:78–84; "Inhibition of tumour necrosis factor–alpha (TNF–alpha) release from mast cells by the anti–inflammatory drugs, sodium cromoglycate and nedocromil sodium."
M. Feldman et al. Annu. Rev. Immunol. 1996 14:397–440 "Role of Cytokines in Rheumatoid Arthritis".
Schmidt H. et al. J. Surg. Res. 1996 63(1):143–146; "Thalidomide inhibits TNF response and increases survival following endotoxin injection in rats."
Kluth D.C., Rees A.J., Semin, Nephrol. 1996, 16:576–582; "Inhibiting inflammatory cytokines."
Chapman P.T. et al., Arthritis Rheum., 1997, 40:955–965; "Endothelial activation in monosodium urate monohydrate crystal–induced inflammation: in vitro and in vivo studies on the roles of tumor necrosis factor alpha and interleukin–1."
Reimund J., Gut 1997, 40;475–480 "In vitro effects of oxpentifylline on Inflammatory Cytokine Release in Patients with Inflammatory Cytokine Release in Patients with Inflammatory Bowel Disease".
Gruschwitz, M., et al., Journal Rheumatology 1997; 24: 1936–43 "In situ Expression and Serum Levels of Tumor Necrosis Factor–α Receptors in Patients with Early Stages of Systemic Sclerosis".

(Continued)

Primary Examiner—Bruck Kifle
(74) Attorney, Agent, or Firm—Darby & Darby

(57) ABSTRACT

The present invention relates to the dibenzoazulene compounds represented by formula I as well as to their pharmaceutical preparations for the inhibition of tumor necrosis factor alpha (TNF-α) and interleukine 1 (IL-1) in mammals at all diseases and conditions where these mediators are excessively secreted. The compounds of the present invention also demonstrate an analgetic action and can be used to relieve pain.

45 Claims, No Drawings

OTHER PUBLICATIONS

Ross S., et al.; Journal of Immunology, 1997, 159:6253–6259, "Suppression on TNFα Expression, Inhibition of TH1 Activity and Amelioration of Collagen–Induced Arthritis by Rolipram".

Gruschwitz, MS et al., J Rheumatol. 1997; "In situ expression and serum levels of tumor necrosis factor–alpha receptors in patients with early stages of systemic sclerosis."

Odeh M. Drugs News Perspect. 11(6) 1998 331–341 "Role of Cytokines in Rheumatoid Arthritis".

Saricaoglu H. et al. Contact Dermatis 1998, 39(5):244–247; "Prevention of nickel–induced allergic contact reations with pentoxifylline."

Ackermann L., Harvima I.T. Arch. Dermatol. Res. 1998, 290:353–359; "Mast cells of psoriatic and atopic dermatitis skin are positive for TNF–α and their degranulation is associated with expression of ICAM–1 in the epidermis."

Stirling D. I. Semin. Cutan. Med. Surg. 1998 17(4):231–242; "Thalidomide and its impact in dermatology."

Peleman R. A., Kips J.C., Pauwels R.A. Clin. Exp. Allergy 1998 28 Suppl.3:53–56; "Therapeutic activities of theophylline in chronic obstructive pulmonary disease."

Kapadia S. et al., Cardiol. Clin., 1998, 16:645–656; "The role of cytokines in the failing human heart."

Liu J.Y. et al., Am. J. Pathol., 1998, 153:1839–1847; "TNF–alpha receptor knockout mice are protected from the fibroproliferative effects of inhaled asbestos fibers."

Cheung A. T. et al., Endocrinology, 1998, 139:4928–4935; "An in vivo model for elucidation of the mechanism of tumor necrosis factor–alpha (TNF–alpha)–induced insulin resistance: evidence for differential regulation of insulin signaling by TNF–alpha."

Liedthe W., An. of Neurology, 1998 vol. 44; 35–46; "Effective Treatment of Models of Multiple Sclerosis by Matrix Metalloproteinase Inhibitors".

Taylor R., Multiple Sclerosis: A Rehabilitive Approach, 1998, 9, 3, 525–536,; "Immunologic Aspects of Multiple Sclerosis".

Oliver S., et al.; Journal of Rheumatology 1998, 25:964–9 "The Effect of Thalidomide and 2 Analogs on Collagen Induced Arthritis".

Matsukawa A., et al.;Lab Invest 1998; 78:559–569. "Analysis of the Cytokine Network Among Tumor Necrosis Factor α Interleukin–1β, Interleukin–8 and Interleukin–1 Receptor Antagonist in Monosodium Urate Crystal–Induced Rabbit Arthritis".

Noguchi,M., et al.; gut 1998, 43:203–209; "Secretion Imbalance between Tumor Necrosis Fact or and its inhibitor in Inflammatory bowel disease".

Shire, MG and Muller GW., Exp. Opin. Ther. Patents. 1998 8(5): 531–544; "TNF–β inhibitors and rheumatoid arthritis".

Arrieta O et al. Int. J. Exp. Pathol. 1999 80(1):11–16; "Protective effect of pentoxifylline plus thalidomide against septic shock in mice."

Sasayama S. et al., Cardiovasc Res. 1999, 42:557–564; "New insights into the pathophysiological role for cytokines in heart Failure."

Dibbs Z. et al., Proc. Assoc. Am. Physicians, 1999, 111:423–428; "Cytokines in heart failure: pathogenetic mechanisms and potential treatment."

Martel–Pelletier J., Allaeddine N. Pelletier JP Front Biosci, 1999 4:D694–703; "Cytokines and their role in the pathophysiology of osteoarthritis."

Rutgeerts P. et al.; Gastroenterology., 1999, 117:761–769; "Efficacy and Safety of Retreatment with Anti–Tumor Necrosis Factor Antibody (Infliximab) to Maintain Remission in Crohn's Disease".

Sandborn W. and Hanauer S., Inflammatory Bowel Diseases 1999, 5(2):119–133; "Antitumor Necrosis Factor Therapy for Inflammatory Bowel Disease; A review of Agents, Pharmacology, Clinical Results and Safety."

Sykes A.P., et al.; Aliment Pharmacol Ther. 1999, 13:1535–1542 "The effect of an inhibitor of matrix metalloproteinases on colonic inflammation in a Erinitrobenzenesulphonic acid rat model of inflammatory bowel disease".

Corral L., et al.; The Journal of Immunology 1999, 163:380–386. "Differential Cytokine Modulation and T Cell Activation by Two Distinct Classes of Thalidomide Analogues That are Potent Inhibitors of TNF–β".

Duong D.J. et al. Arch. Dermatol. 1999 135 (9):1079–1087; "American experience with low–dose thalidomide therapy for severe cutaneous lupus erythematosus."

Maini R.N, Taylor P.C. Annu. Rev. Med. 2000 51:207–229 "Anti–Cytokine Therapy for Rheumatoid Arthritis".

Westacott C.I. et al. Osteoarthritis Cartilage 2000 8(3):213–221; "Tumor necrosis factor alpha can contribute to focal loss of cartilage in osteoarthritis".

Wim B van den Berg, Ph.D. Arthritis Res 2001, 3:18–26; "Anti–Cytokine Therapy in Chronic Destructive Arthritis".

Heilig B et al., Z Rheumatol. Nov.–Dec. 1993;52(6):383–9, "[Expression of TNF receptors in rheumatoid arthritis and ankylosing spondylitis]" [Article in German].

Krakauer T, Stiles BG Clin Diagn Lab Immunol. Jul. 1999;6(4):594–8. Pentoxifylline inhibits superantigen–induced toxic shock and cytokine release.

Guidance for Industry and Reviewers, U.S. Department of Health and Human Services, Food and Drugs Administration, Center for Drug Evaluation and Research, Center for Biologics Evaluation and Research, Dec. 2002.

* cited by examiner

THIENODIBENZOAZULENE COMPOUNDS AS TUMOR NECROSIS FACTOR INHIBITORS

This is a Continuation-In-Part of PCT/HR01/00027 filed May 16, 2001, which designated the United States, entire disclaimer of which is incorporated herein by reference.

TECHNICAL FIELD

The present invention relates to new derivatives of 1-thiadibenzoazulene, their pharmacologically acceptable salts, solvates and prodrug forms, processes for the preparation thereof and their antiinflammatory effects and particularly to the inhibition of the production of the tumor necrosis factor-α (TNF-α) and of interleukin-1 (IL-1) and to their analgetic action.

PRIOR ART

Hitherto, 1-thiadibenzoazulenes, which are substituted in position 2 with a methyl, methyl ketone, nitro group or a derivative of a carboxylic group (Cagniant P, and Kirsch G., C. R. Hebd. *Sciences Acad. Sci.*, 1976, 283:638–686) have been described in the literature. According to our knowledge and available literature data, however, neither 1-thiadibenzoazulene derivatives of general formula I nor any possible methods of their preparation have previously been described. It is also not known that 1-thiadibenzoazulenes possess an anti-inflammatory effect.

In 1975 TNF-α was defined as an endotoxine-induced serum factor causing tumor necrosis in vitro and in vivo (Carswell E. A. et al., *Proc. Natl. Acad. Sci. U.S.A.* 1975, 72:36666–3670). In addition to antitumor activity, TNF-α has several other biologic activities, which are important in the homeostasis of organism as well as in pathophysiological conditions. The main sources of TNF-α are monocytes-macrophages, T-lymphocytes and mast cells.

The finding that anti-TNF-α antibodies (cA2) are effective in the treatment of patients suffering from rheumatoid arthritis (RA) (Elliott M. et al., Lancet 1994, 344:1105–1110) intensified the interest to find new TNF-α inhibitors as possible potent medicamepts for RA. Rheumatoid arthritis is an autoimmune chronic inflammatory disease characterized by irreversible pathological changes of the joints. In addition to RA, TNF-α antagonists are also applicable to several pathological conditions and diseases such as spondylitis, osteoarthritis, gout and other arthritic conditions, sepsis, septic shock, toxic shock syndrome, atopical dermatitis, contact dermatitis, psoriasis, glomerulonephritis, lupus erhythematosus, seleroderma, asthma, cachexia, chronic obstructive lung disease, congestive heart failure, insulin resistance, lung fibrosis, multiple sclerosis, Crohn's disease, ulcerative colitis, viral infections and AIDS.

Proof of biological importance of TNF-α was obtained in in vivo experiments in mice having inactivated genes for TNF-α or its receptor. Such animals were resistant to collagen-induced arthritis (Mori L. et al., *J. Immunol.* 1996, 157:3178–3182) and to endotoxin-induced shock (Pfeffer K. et al., *Cell* 1993, 73:457–467). In experiments with animals having an increased TNF-α level a chronic inflammatory polyarthritis appeared (Georgopoulos S. et al., *J. Inflamm.* 1996, 46:86–97; Keffer J. et al., *EMBO J.* 1991, 10:4025–4031), which was palliated by inhibitors of TNF-α production. The treatment of such inflammatory and pathologic conditions usually includes the application of non-steroid antiinflammatory medicaments, in severe cases, however, gold salts, D-penicillinamine or methotrexate are administered. Said medicaments act symptomatically and do not stop the pathological process. New approaches in theraphy of rheumatoid arthritis have been established upon medicaments such as tenidap, leflunomide, cyclosporine, FK-506 and biomolecules neutralizing the activity of TNF-α. Presently, the fission protein of the soluble TNF receptor named etanercept (Enbrel, Immunex/Wyeth) and mouse and human cimeric monoclonal antibody named infliximab (Remicade, Centocor) are available on the market. In addition to RA-therapy, etanercept and infliximab are also approved for the treatment of Chron's disease (*Exp. Opin. Invest Drugs* 2000, 9, 103).

In RA-therapy, in addition to the inhibition of TNF-α secretion, it is also important to inhibit IL-1 secretion since IL-1 represents an important cytokine in cell regulation, immunoregulation and in the pathophysiological conditions such as inflammation (Dinarello C. A. et al., Rev. Infect. Disease, 1984, 6:51). Known biological activities of IL-1 are: activation of T-cells, induction of elevated temperature, stimulation of prostaglandin or collagenase secretion, chemotaxis of neutrophils and reduction of iron level in plasma (Dinarello C. A., J. Clinical Immunology, 1985, 5:287). There are two known receptors to which IL-1 can be bound: IL-1RI and I-1RII. IL-1RI transfers the signal intracellularly, while IL-1RII is present on the cell surface and does not transfer the signal within the cell. Since IL1-RII binds both IL-1 and IL1-RI, it can act as a negative regulator of IL-1 effect. In addition to the mentioned mechanism of regulation of signal transfer, another natural IL-1 receptor antagonist (IL-1ra) is present in cells. This protein binds to IL-1RI but does not transfer any signal. Yet its potency in the inhibition of signal transfer is not great, therefore it must be present in a 500 times higher concentration than IL-1 in order to break the signal transfer. Recombinant human IL-1ra (Amgen) was clinically tested (Bresnihan B. et al., Arthrit. Rheum. 1996, 39:73) and the results obtained demonstrated an improvement of the symptoms in 472 patients suffering from RA with respect to a placebo. These results indicate the importance of inhibition of IL-1 activity in the treatment of diseases such as RA where the production of IL-1 is increased.

According to the known and established prior art, 1-thiadibenzoazulene compounds representing the subject of the present invention, their pharmacologically acceptable salts, hydrates, prodrug forms and pharmaceutical preparations comprising them have hitherto not been described. Moreover, no compound representing the subject of the present invention has been described either as an anti-inflammatory substance or as an inhibitor of TNF-α and IL-1 secretion or an analgetic.

Technical Solution

The present invention relates to compounds represented by the general formula I, 1-thiadibenzoazulene derivatives, to their pharmacologically acceptable salts and solvates represented by formula I

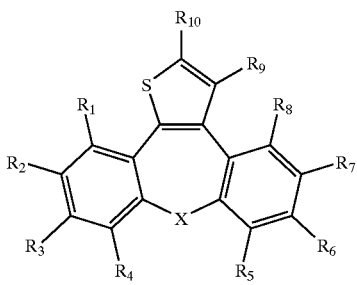

I wherein

X can represent $CH_2$ or a heteroatom such as O, S, S(=O), S(=O)$_2$ or $NR_{13}$ wherein $R_{13}$ means hydrogen, $C_{1-6}$ alkyl, $C_{1-6}$ alkylcarbonyl, arylcarbonyl, $C_{1-6}$ alkylsulfonyl or arylsulfonyl and $R_1$, $R_2$, $R_3$, $R_4$, $R_5$, $R_6$, $R_7$, $R_8$, $R_9$ independently from each other represent substituents that can be hydrogen, halogen (fluorine, chlorine or bromine); or $C_1$–$C_7$ alkyl, alkenyl, aryl or heteroaryl; or can represent different groups: halomethyl, hydroxy, $C_1$–$C_7$ alkoxy or aryloxy, $C_1$–$C_7$ alkylthio or arylthio, $C_1$–$C_7$ alkylsulfonyl, cyano, amino, mono- and di-$C_1$–$C_7$ substituted amino, derivatives of carboxylic group ($C_1$–$C_7$ carboxylic acids and their anhydrides, $C_1$–$C_7$ unsubstituted, mono-, di-substituted amides, $C_1$–$C_7$ alkyl or aryl esters), $C_1$–$C_7$ derivatives of carbonyl group ($C_1$–$C_7$ alkyl or aryl carbonyls), and $R_{10}$ can represent substituents such as: $C_2$–$C_{15}$ alkyl, $C_2$–$C_{15}$ alkenyl, $C_2$–$C_{15}$ alkyl, alkenyl, aryl or heteroaryl, $C_1$–$C_{15}$ is haloalkyl, $C_1$–$C_{15}$ hydroxyalkyl, $C_1$–$C_{15}$ alkyloxy, $C_1$–$C_{15}$ alkylthio, $C_3$–$C_{15}$ alkylcarbonyl, $C_2$–$C_{15}$ alkylcarboxylic acid, $C_2$–$C_{15}$ alkylesters, $C_1$–$C_{15}$ alkylsulfonyl, $C_1$–$C_{15}$ alkylarylsulfonyl, arysulfonyl and $C_1$–$C_{15}$ alkylamino represented by the general formula —$(CH_2)_n$-A wherein n means 1–15, and one or more methylene groups can be substituted with an oxygen or sulfur atom, and A represents a five- or six-membered, saturated or unsaturated ring with one, two or three heteroatoms, or

wherein $R_{11}$ and $R_{12}$ independently from each other represent hydrogen, $C_1$–$C_7$ alkyl, alkenyl, alkynyl, aryl or heteroaryl, or a heterocycle with 1–3 heteroatoms.

The terms as used in the present invention are defined as stated below unless otherwise specified.

"Alkyl" means a monovalent alkane (hydrocarbon), wherefrom a radical is derived, which can be a straight-chain, a branched-chain or a cyclic hydrocarbon or a combination of straight-chain and cyclic hydrocarbons and of branched-chain and cyclic hydrocarbons. The preferred straight-chain or branched-chain alkyls include methyl, ethyl, propyl, iso-propyl, butyl, sec-butyl and t-butyl. The preferred cycloalkyls include cyclopentyl and cyclohexyl. Alkyl also represents a straight-chain or branched-chain alkyl group containing a cycloalkyl portion or being broken by it.

"Alkenyl" means a hydrocarbon radical being a straight-chain, a branched-chain or a cyclic hydrocarbon or a combination of straight-chain and cyclic hydrocarbons and of branched-chain and cyclic hydrocarbons, which has at least one double carbon-carbon bond. Particularly ethenyl, propenyl, butenyl and cyclohexenyl are meant. As stated above under the definition of "alkyl", also alkenyl can be a straight-chain, a branched-chain or a cyclic one, and a portion of alkenyl group can contain double bonds and it can also be substituted when a substituted alkenyl group is of interest. Alkenyl also represents a straight-chain or a branched-chain alkenyl group containing a cycloalkenyl portion or being broken by it.

"Alkynyl" means a hydrocarbon radical, which is a straight-chain or a branched-chain one and contains at least one and at most three triple carbon-carbon bonds. Particularly ethenyl, propenyl and butenyl groups are meant.

"Aryl" means an aromatic ring such as phenyl, substituted phenyl or similar groups as well as fused rings such as naphthyl etc. Aryl contains at least one ring with at least 6 carbon atoms or two rings having together 10 carbon atoms and alternating double (resonant) bonds between carbon atoms (particularly phenyl and naphthyl). Aryl groups can be additionally substituted with one or two substituents such as halogens (fluorine, chlorine and bromine), hydroxy, $C_1$–$C_7$ alkyls, $C_1$–$C_7$ alkoxy or aryloxy, $C_1$–$C_7$ alkylthio or arylthio, alkylsulfonyl, cyano or amino groups.

"Heteroaryl" means a monocyclic or a bicyclic aromatic hydrocarbon containing at least one heteroaom such as O, S or N with carbon and nitrogen representing the binding sites for the basic formula. Heteroaryl can be additionally substituted with a halogen or $CF_3$ group and a lower alkyl such as methyl, ethyl or propyl. Heteroaryl means an aromatic and a partly aromatic group with one or more heteroatoms. Examples of this type are thiophene, pyrrole, imidazole, pyridine, oxazole, thiazole, pyrazole, tetrazole, pyrimidine, pyrazine and triazine.

Another object of the present invention relates to a process for the preparation of dibenzoazulene derivatives represented by formula I. These compounds can be prepared from thiophene esters of the general formula I, wherein all radicals and symbols have the above-defined meanings i.e. where radicals $R_1$, $R_2$, $R_3$, $R_4$, $R_5$, $R_6$, $R_7$, $R_8$ and $R_9$ have the above-defined meanings and $R_{10}$ means ethoxycarbonyl (Cagniant P. and Kirsch G., *C. R. Hebd. Sceances Acad. Sci.*, 1976, 283:683–686). By means of further reactions these esters are converted into other substituents defined as $R_{10}$. These reactions include the reduction of an ester to the corresponding alcohol or aldehyde, alkylation and other nucleophilic reactions on the ethoxycarbonyl group (Scheme 1).

Scheme 1

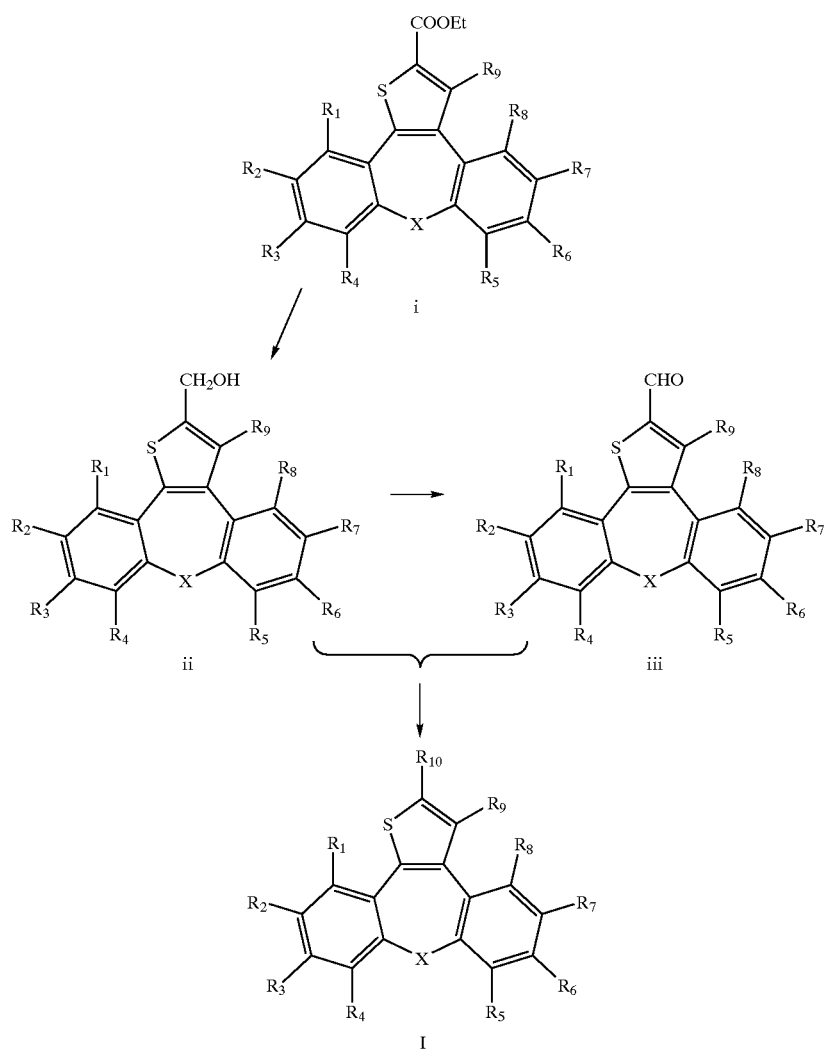

The reduction of the ethoxycarbonyl group is performed by the use of metal hydrides to obtain an alcohol ($R_{10}$= hydroxymethyl). The reaction is performed in suitable non-polar solvents (preferably in aliphatic ethers) at a temperature from 0 to 36° C. within a period of 1 to 5 hours. The isolation and purification of the compounds can be performed by recrystallization or column chromatography.

By the reaction of an alcohol of the general formula I wherein $R_{10}$ represents hydroxymethyl and of a chloride of the formula II $$Cl\text{—}(CH_2)_n\text{-}A \qquad II$$

wherein the symbols n and A have the above-defined meanings, ω-amino ethers of the general formula I are obtained.

The stated reactions are performed at a temperature from 20 to 100° C. within a period of 1 to 24 hours under the conditions of phase-transfer catalysis in a two-phase system (preferably 50% NaOH-toluene) and in the presence of a phase-transfer catalyst (preferably benzyl-triethyl-ammonium-chloride, benzyl-triethyl-ammonium-bromide, cetyl-trimethyl-bromide). Subsequently to the treatment of the reaction mixture, the obtained products are isolated by recrystallization or chromatography on a silica gel column.

By the oxidation of an alcohol of the general formula I wherein $R_{10}$-hydroxymethyl with pyridinyl dichromate or pyridinyl chlorochromate, an aldehyde the general formula I wherein $R_{10}$=CHO is obtained. The reaction is performed in dichloromethane at room temperature within a period of 2 to 5 hours. The obtained aldehyde is purified by passing through a column of florisil or silica gel.

The reaction of an aldehyde of the general formula I wherein $R_{10}$=CHO with different corresponding phosphorus-ylides results in the formation of compounds of the general formula I, wherein $R_{10}$ has the above-defined meanings and which have an alkene functionality in the position 2 of the chain defining $R_{10}$. These reactions are performed in anhydrous solvents such as toluene, benzene or hexane at the reflux temperature of the solvent within a period of 3 to 5 hours. The obtained products are purified by column chromatography.

By the hydrogenation of the compounds I, wherein $R_{10}$ contains one or more double carbon-carbon bonds, compounds of the general formula I wherein $R_{10}$ has a saturated chain are obtained. These reactions are usually performed with 5% Pd on active charcoal under a hydrogen pressure from $6.7 \times 10^4$ to $4.0 \times 10^5$ Pa in ethanol, ethyl acetate or other suitable solvents. By filtration and evaporation of the solvents saturated products are obtained, which can be purified to the desired purity by recrystallization or column chromatography on silica gel.

The pharmaceutically suitable salts of the compounds representing a subject of the present invention include salts with inorganic acids (hydrochloric, hydrobromic, phosphoric, metaphosphoric, nitric and sulfuric acids) or organic acids (tartaric, acetic, trifluoroacetic, citric, maleic, lactic, fumaric, benzoic, succinic, methanesulfonic and p-toluenesulfonic acids).

A further subject of the present invention is the use of the compounds of the present invention in the treatment of inflammatory diseases and conditions, particularly of all diseases and conditions induced by an excessive secretion of TNF-α and IL-1.

An effective dose of the cytokine or inflammation mediator production inhibitors of the present invention or of pharmaceutically acceptable salts thereof is useful in the production of medicaments for the treatment and prophylaxis of any pathological condition or disease induced by an excessive unregulated production of cytokines or inflammation mediators.

More specifically, the present invention relates to an effective dose of TNF-α inhibitors, which can be determined by common methods.

Further, the present invention relates to pharmaceutical preparations containing an effective nontoxic dose of compounds of the present invention as well as pharmaceutically acceptable carriers and solvents.

The preparation of the pharmaceutical preparations can include mixing, granulating, tabletting and dissolving the ingredients. Chemical carriers can be in solid or liquid form. Solid carriers can be lactose, sucrose, talc, gelatine, agar, pectin, magnesium stearate, fatty acids etc. Liquid carriers can be syrups, oils such as olive, sunflower seed or soybean oils, water etc. Similarly, carriers may also contain a component for a sustained release of the active component such as glyceryl monostearate or glyceryl distearate. Several forms of pharmaceutical compositions can be prepared. If a solid carrier is used these forms can include tablets, solid gelatinous capsules, powders or granules that can be administered orally in capsules. The amount of the solid carrier can vary but mainly it is in the range from 25 mg to 1 g. If a liquid carrier is used, the preparation can be in the form of a syrup, emulsion, soft gelatinous capsules, sterile injectable liquids such as ampules, or nonaqueous liquid suspensions.

The compounds of the present invention can be administered orally, parenterally, topically, intranasally, intrarectally and intravaginally. "Parenterally" means intraveneous, intramuscular and subcutaneous administrations. The corresponding preparations of the compounds of the present invention can be used in the prophylaxis as well as in the treatment of several diseases and pathological inflammatory conditions caused by an excessive nonregulated production of cytokines or inflammation mediators, foremost TNF-α. They include rheumatoid arthritis, rheumatoid spondylitis, osteoarthritis and other arthritic pathological conditions and diseases, eczema, psoriasis as well as other inflammatory conditions of the skin such as burns induced by UV radiation (sun rays and similar UV sources), inflammatory eye diseases, Crohn's disease, ulcerative cholitis and asthma.

The inhibitory effect of the compounds of the present invention on the secretion of TNT-α and IL-1 was determined by the following in vitro and in vivo experiments:
Determination of TNF-α and IL-1 Secretion in Mononuclear Cells of Human Peripheral Blood in Vitro Peripheral blood mononuclear cells (PMBC) were prepared from heparinized whole blood after separation of PMBC on Ficoll-Hypaque (Amersham-Pharmacia). For the determination of TNF-α level $3.5–5 \times 10^4$ cells were cultured in a total volume of 200 μl within a period of 18 to 24 hours on microtiter flat bottom plates (96 wells, Falcon) in RPMI 1640 medium supplemented with 10% of heat-inactivated human AB serum (Hrvatski zavod za transfuzijsku medicinu, Zagreb), 100 units/ml of penicillin, 100 mg/ml of streptomycine and 20 mM HEPES (GIBCO). The cells were incubated at 37° C. in an atmosphere with 5% $CO_2$ and 90% moisture. The cells in a negative control were cultured only in the medium (NC), while the secretion of TNF-α in a positive control was stimulated by the addition of 1 μg/ml lipopolysaccharide (LPS, *E. coli* serotype 0111:B4, SIGMA) (PC) and the effect of the tested substances on TNF-α secretion was tested after their addition to cell cultures stimulated with LPS (TS). The TNF-α level in the cell supernatant was determined by ELISA according to the manufacturer's (R&D Systems) suggestions. The test sensitivity was <3 pg/ml TNF-α. The determination of IL-1 level was performed as described for TNF-α determination, only that $1 \times 10^5$ cells/well and 0.1 ng/ml of LPS were used. IL-1 level was determined by ELISA (R&D Systems). The percentage inhibition of TNF-α or IL-1 production was calculated by the following equation:

% inhibition=[1−(TS−NC)/(PC−NC)]*100.

IC-50 value was defined as the concentration of the substance at which 50% of TNF-α production was inhibited. The compounds demonstrating IC-50 in concentrations of 20 μM or lower were considered active.

Determination of TNF-α and IL-1 Secretion by Mouse Peritoneal Macrophages in Vitro For obtaining peritoneal macrophages, male BALB/c mice at an age of 8 to 12 weeks were injected i.p. with 300 μg of zimozane (SIGMA) dissolved in a phosphate buffer (PBS) in a total volume of 0.1 ml/mouse. After 24 hours the mice were subjected to euthanasia according to the Laboratory Animals Welfare Act. The peritoneal cavity was washed with 5 ml of sterile saline. The obtained peritoneal macrophages were washed twice with sterile saline and after the last centrifugation (800 g) they were resuspended in RPMI 1640. For the determination of TNF-α secretion, $5 \times 10^4$ cells/well were cultured in a total volume of 200 μl within a period of 18 to 24 hours on microtiter flat bottom plates (96 wells, Falcon) in RPMI 1640 medium supplemented with 10% of heat-inactivated fetal calf serum (FCS), 100 units/ml of penicillin, 100 mg/ml of streptomycine, 20 mM HEPES and 50 μM 2-β mercaptoethanol (all of GIBCO). The cells were incubated at 37° C. in an atmosphere with 5% $CO_2$ and 90% moisture. The cells in a negative control were cultured only in the medium (NC), while the secretion of TNF-α in a positive control was stimulated by the addition of 1 μg/ml lipopolysaccharide (LPS, *E. coli* serotype 0111:B4, SIGMA) (PC) and the effect of the tested substances on TNF-α secretion was tested after their addition to cell cultures stimulated with LPS (TS). The TNF-α level in the cell supernatant was determined by ELISA according to manufacturer's (R&D Systems, Biosource) suggestions. The determination of IL-1 level was performed as described for TNF-α determination, only that $1 \times 10^5$ cells/well and 0.1 ng/ml of LPS were used. The IL-1 level was determined by ELISA (R&D Systems). The percentage inhibition of TNF-α or IL-1 production was calculated by the following equation:

% inhibition=[1−(TS−NC)/(PC−NC)]*100.

IC-50 value was defined as the concentration of the substance at which 50% of TNF-α production was inhibited. The compounds demonstrating IC-50 in concentration of 10 μM or lower were considered active.

In Vivo Model of LPS-Induced Exccessive Secretion of TNF-α or IL-1 in Mice

TNF-α or IL-1 secretion in mice was induced according to the previously described method (Badger A. M. et al., *J. of Pharmac. and Env. Therap.* 1996, 279:1453–1461). In the test male BALB/c mice at an age of 8 to 12 weeks in groups of 6 to 10 animals were used. Animals were treated p.o. either only with the solvent (in a negative and a positive control) or with solutions of the substance 30 minutes prior to the i.p. treatment with LPS (*E.coli* serotype 0111:B4, Sigma) in a dose of 25 μg/animal. Two hours later the animals were euthanized by means of an i.p. injection of Roumpun (Bayer) and Ketanest (Park-Davis). A blood sample from each animal was collected in a "vacutaner" tube (Becton Dickinson) and the plasma was separated according to the manufacturer's suggestions. The TNF-α level in the plasma was determined by ELISA (Biosource, R&D Systems) according to the process prescribed by the manufacturer. The test sensitivity was <3 pg/ml TNF-α. The IL-1 level was determined by ELISA (R&D Systems). The percentage inhibition of TNF-α or IL-1 production was calculated by the following equation:

% inhibition=[1−(TS−NC)/(PC−NC)]*100.

The compounds demonstrating a 30% or higher inhibition of TNF-α production at a dose of 10 mg/kg were considered active.

Writhing Test for Analgetic Activity

In this test, pain is induced with an injection of an irritant, usually acetic acid, into the peritoneal cavity of mice. The animals respond by the characteristic writhings, which gave the name of the test. (Collier H, O. J. et al., *Pharmac. Chemother.*, 1968, 32:295–310; Fukawa K. et al., *J. Pharmacol. Meth.*, 1980, 4:251–259; Schweizer A. et al, *Agents Actions*, 1988, 23:29–31). This test is suitable for the determination of analgetic activity of compounds. Process: male BALB/c mice (Charles River, Italy) at an age of 8 to 12 weeks were used. To a control group methyl cellulose was administered p.o. 30 minutes prior to i.p. administration of acetic acid in a concentration of 0.6%, whereas to the test groups a standard (acetyl salicylic acid) or test substances in methylcellulose were administered p.o. 30 minutes prior to i.p. administration of 0.6% acetic acid (volume 0.1 ml/10 g). Mice were individually placed under glass funnels und the number of writhings of each animal was recorded during a period of 20 minutes. The percentage inhibition of writhings was calculated according to the equation:

% inhibition=(mean value of number of writhings in the control group−number of writhings in the test group)/number of writhings in the control group* 100.

The compounds demonstrating the same or better analgetic activity than acetyl salicylic acid were considered active.

In vivo Model of LPS-Induced Shock in Mice

Male BALB/c mice at an age of 8 to 12 weeks (Charles River, Italy) were used. LPS isolated from *Serratie marcessans* (Sigma, L-6136) was diluted in sterile saline. The first LPS injection was administered intradermally in a dose of 4 μg/mouse. 18 to 24 hours later LPS was administered i.v. in a dose of 200 μg/mouse. To a control group two LPS injections were administered in the above described manner. The test groups were administered the substances p.o. half an hour prior to each LPS administration. The survival after 24 hours was observed.

The compounds resulting in a 40% or better survival at a dose of 30 mg/kg were considered active.

The compounds of Examples 1, 5, 19 and 21 demonstrate activity in at least two investigated tests. These results, however, only illustrate the biological activity of the compounds and do not limit the present invention in any way.

PREPARATION PROCESSES WITH EXAMPLES

The present invention is illustrated but in no way limited by the following Examples.

Preparation of Alcohol

Method 1

To a suspension of $LiAlH_4$ in dry ether (10 mmole/15 ml of dry ether) an ether solution of an ester (2 mmole/15 ml dry ether) was added dropwise. The reaction mixture was stirred at room temperature for 4 hours. Subsequently, when all ester was consumed in the reaction (the course of the reaction was followed by thin layer chromatography), the excess of $LiAlH_4$ was decomposed by the addition of diethyl ether and water. The obtained white precipitate was filtered off and, after drying over anhydrous $Na_2SO_4$, the filtrate was evaporated under the reduced pressure. The crude product was purified by column chromatography.

Method 2 ($R_{10}$=—CH=$CHCH_2OH$)

To a dichloromethane solution of α,β-unsaturated ester (5 mmole/10 ml of dry dichloromethane) cooled to −10° C., diisobutylaluminum hydride (5 mmole) was added. The reaction mixture was stirred for 30 minutes at 0° C. and then for 2 hours at room temperature. Then methanol and potassium-sodium tartrate were added into the reaction mixture and the obtained products were extracted with diethyl ether. By column chromatography pure products were isolated.

According to the process of preparing an alcohol and starting from corresponding esters, dibenzoazulene alcohols represented by the formula I, wherein $R_1$, $R_5$, $R_7$, $R_8$ and $R_9$=H, and $R_2$, $R_3$, $R_4$, $R_6$, $R_7$, $R_{13}$ and X have the meanings as illustrated in Table 1, were prepared.

TABLE 1

| Comp. | X | $R_2$ | $R_3$ | $R_4$ | m.p. (° C.) | $^1H$ NMR (ppm, $CDCl_3$) |
|---|---|---|---|---|---|---|
| 1 | O | H | H | H | 120–122 | 2.13(s, 1H); 4.85(s, 2H); 7.12–7.43(m, 9H) |
| 2 | O | H | H | Cl | 131–133 | 1.88(s, 1H); 4.94(s, 2H); 7.1–7.6(m, 8H) |
| 3 | O | Cl | H | H | 157–158 | 1.72(s, 1H); 4.91(s, 2H); 7.2–7.5(m, 8H) |
| 4 | O | F | H | H | 117–123 | 1.74(s, 1H); 4.91(s, 2H); 7.0–7.46(m, 8H) |
| 5 | S | H | H | H | — | 2.14(s, 1H); 4.88(s, 2H); 7.2–7.6(m, 9H) |
| 6 | S | F | H | H | 124–128 | 1.79(s, 1H); 4.93(s, 2H); 6.9–7.6(m, 8H) |
| 7 | S | Cl | H | H | 122 | 1.96(s, 1H); 4.92(s, 2H); 7.2–7.6(m, 8H) |
| 8 | S | Br | H | H | — | 1.77(s, 1H); 5.01(s, 2H); 7.3–7.7(m, 8H) |

TABLE 1-continued

| | X | R$_2$ | R$_3$ | R$_4$ | R$_6$ | R$_{13}$ | | $^1$H NMR (ppm, CDCl$_3$), MS (m/z) |
|---|---|---|---|---|---|---|---|---|
| 9 | S | H | CF$_3$ | H | | — | | 3.3(s, 1H); 4.95(s, 2H); 7.32–7.57(m, 4H); 7.59 (s, 1H); 7.62–7.66(m, 2H); 7.9(s, 1H) |
| 10 | S | H | Cl | H | | — | | 1.75(s, 1H); 4.92(s, 2H); 7.23–7.66(m, 8H) |
| 11 | S | H | Br | H | | — | | 1.67(s, 1H); 4.93(s, 2H); 7.23–7.81(m, 8H) |

| Comp | X | R$_2$ | R$_3$ | R$_4$ | R$_6$ | R$_{13}$ | R$_{10}$ | $^1$H NMR (ppm, CDCl$_3$), MS (m/z) |
|---|---|---|---|---|---|---|---|---|
| 12 | S | CH$_3$ | H | CH$_3$ | H | — | CH$_2$OH | 1.8(s, 1H); 2.29(s, 3H); 2.61(s, 3H); 4.91(s, 2H); 7.1(s, 1H); 7.18(s, 1H); 7.22(s, 1H); 7.27–7.71(m, 4H) |
| 13 | S | Cl | Cl | H | H | — | CH$_2$OH | 1.72(s, 1H); 4.94(s, 2H); 7.24(s, 1H); 7.29–7.54(m, 3H), 7.58(s, 1H), 7.60–7.65(m, 1H); 7.74(s, 1H) |
| 14 | S | F | H | Cl | H | — | CH$_2$OH | 2.07(s, 1H); 4.96(s, 2H); 6.96–7.96 (m, 7H) |
| 15 | O | H | H | H | H | — | (CH$_2$)$_3$OH | 1.54(s, 1H); 2.03(m, 2H); 3.01(t, 2H); 3.79(t, 2H); 7.08(s, 1H); 7.13–7.46(m, 8H) |
| 16 | S | H | H | H | H | — | (CH$_2$)$_3$OH | 1.69(s, 1H); 2.04(m, 2H); 2.99(t, 2H); 3.78(t, 2H), 7.04(s, 1H); 7.21–7.66(m, 8H) |
| 17 | CH$_2$ | H | H | H | H | — | CH$_2$OH | 1.95(s, 1H); 3.75(m, 2H); 4.92(s, 2H); 7.20–7.60(m, 9H) |
| 18 | S | H | H | H | H | — | CH=CHCH$_2$OH | 2.03(s, 1H), 4.33(dd, 1H), 6.3(dt, 1H); 6.78(d, 1H); 7.15–7.75(m, 9H) |
| 19 | N | H | H | H | H | CH$_2$C$_6$H$_5$ | CH$_2$OH | 1.5–2.0(bs, 1H); 4.97(s, 2H); 4.99(d, 2H), 7.05–7.42(m, 14H) |
| 20 | S | SCH$_3$ | H | H | H | — | CH$_2$OH | 1.8(s, 1H), 2.47(s, 3H), 4.92(s, 2H), 7.15–7.65(m, 8H) |
| 21 | S | H | CH$_3$ | H | H | — | CH$_2$OH | 1.8(s, 1H); 2.34(s, 3H); 4.92(s, 2H); 7.15–7.65(m, 8H) |
| 22 | S | CH$_3$ | H | H | H | — | CH$_2$OH | 2.33(s, 3H), 4.90(s, 2H), 7.11–7.63(m, 8H) |
| 23 | O | H | OCH$_3$ | H | H | — | CH$_2$OH | MS: m/z 333 2(M$^+$ + Na); 293(M − OH) |
| 24 | S | H | H | H | Cl | — | CH$_2$OH | 1.67(s, 1H), 4.93(s, 2H), 7.19–7.65 (m, 8H) |
| 25 | N | H | H | H | H | COC$_6$H$_5$ | CH$_2$OH | 2.82(bs, 1H); 4.81(s, 2H), 7.00–7.60 (m, 14H) |
| 26 | N | H | H | H | H | H | CH$_2$OH | DMSO 4.65(s, 2H); 5.59(bs, 1H); 6.90–7.31(m, 9H) |
| 27 | S | H | F | H | H | — | CH$_2$OH | 1.76(s, 1H); 4.92(s, 2H); 7.0–7.65(m, 8H) |

The compounds decribed in Examples 1–5 were prepared from alcohol 1 and the corresponding chloroalkyl-dialkyamine hydrochloride according to the process described in Example 1.

Example 1

Dimethyl-[3-(8-oxa-1-thia-dibenzo[e,h]azulene-2-ylmethoxy)-propyl]-amine hydrochloride To a solution of 3-dimethylaminopropylchloride hydrochloride (2.2 g, 0.014 mole) in 50% sodium hydroxide (5 ml), benzyltriethylammonium chloride (0.1 g, 0.44 mmole) and a toluene solution of alcohol 1 (0.28 g, 0.001 mole) were added. The reaction mixture was heated under vigorous stirring and reflux for 4 hours. Then it was cooled to room temperature, diluted with water and extracted with dichloromethane. After purification by column chromatography an oily product (0.25 g) was isolated. By the addition of concentrated hydrochloric acid into the cold ethanol solution of amine, a crystalline product, m.p. 162–165° C., was obtained.

C, H, N, S analysis: C, 65.45 (calc. 65.74); H, 6.12 (calc. 6.02); N, 3.89 (calc. 3.48); S 8.52 (calc. 7.98) $^1$H NMR (ppm, CDCl$_3$): 2.18 (m, 2H); 2.79 (d, 6H); 3.15 (m, 2H); 3.68 (t, 2H); 4.71 (s, 2H); 7.15–7.58 (m, 9H), 12.29 (s, 1H).

Example 2

Dimethyl-[2-(8-oxa-1-thia-dibenzo[e,h]azulene-2-ylmethoxy)-ethyl]-amine hydrochloride By the reaction of alcohol 1 (0.45 g, 0.0015 mole) and 2-dimethylaminoethylchloride hydrochloride (3.05 g, 0.021 mole), an oily product (0.3 g) was obtained, which was converted into the hydrochloride, m.p. 203° C.

C, H, N analysis: C, 64.85 (calc. 65.02); H, 5.80 (calc. 5.72); N, 3.48 (calc. 3.61). $^1$H NMR (ppm, CDCl$_3$): 2.89 (s, 6H); 3.27 (m, 2H); 4.07 (m, 2H); 4.78 (s, 2H); 7.16–7.47 (m, 9H); 12.5 (s, 1H).

Example 3

4-[2-(8-oxa-1-thia-dibenzo[e,h]azulene-2-ylmethoxy)-ethyl]-morpholine hydrochloride By the reaction of alcohol 1 (0.45 g, 0.0015 mole) and 4-(2-chloroethyl)-morpholine hydrochloride (3.9 g, 0.021 mole), an oily product (0.34 g) was obtained, which was converted into the hydrochloride, m.p. 164° C.

C, H, N analysis: C, 63.57 (calc. 64.25); H, 5.76 (calc. 5.6); N, 3.79 (calc. 3.26). $^1$H NMR (ppm, CDCl$_3$): 2.99 (bs, 2H); 3.23 (m, 2H); 3.55 (d, 2H); 3.94 (d, 2H); 4.14 (m, 2H); 4.27 (m, 2H); 4.75 (s, 2H); 7.14–7.44 (m, 9H); 13.16 (s, 1H).

Example 4

1-[2-(8-oxa-1-thia-dibenzo[e,h]azulene-2-ylmethoxy)-ethyl]-piperidine hydrochloride By the reaction of alcohol 1 (0.45 g, 0.0015 mole) and 1-(2-chloroethyl)-piperidine monohydrochloride (3.86 g, 0.021 mole), an oily product (0.48 g) was obtained, which was converted into the hydrochloride, m.p. 179° C.

C, H, N analysis: C, 67.53 (calc. 67.35); H, 6.30 (calc. 6.12); N, 3.61 (calc. 3.27). $^1$H NM (ppm, CDCl$_3$): 1.83 (m, 4H); 2.25 (m, 2H); 2.74 (m, 2H); 3.18 (m, 2H); 3.6 (m, 2H); 4.10 (m, 2H); 4.73 (s, 2H); 7.13–7.5 (m, 9H); 12.15 (s, 1H).

Example 5

1-[2-(8-oxa-1-thia-dibenzo[e,h]azulene-2-ylmethoxy)-ethyl]-pyrrolidine hydrochloride By the reaction of alcohol 1 (0.45 g, 0.0015 mole) and 1-(2-chloroethyl)-pyrrolidine hydrochloride (3.6 g, 0.021 mole), an oily product (0.41 g) was obtained, which was converted into the hydrochloride, m.p. 203–205° C.

C, H, N analysis: C, 67.12 (calc. 67.35); H, 6.03 (calc. 5.84); N, 3.91 (calc. 3.38). $^1$H NMR (ppm, CDCl$_3$): 2.02 (m, 2H); 2.18 (m, 2H); 2.91 (m, 2H); 3.27 (m, 2H); 3.81 (m, 2H); 4.08 (m, 2H); 4.75 (s, 2H); 7.12–7.5 (m, 9H); 12.7 (s, 1H).

The compounds described in Examples 6–10 were prepared from alcohol 2 and the corresponding chloroalkyl-dialkylamine hydrochloride according to the process described in Example 6.

Example 6

[3-(9-chloro-8-oxa-1-thia-dibenzo[e,h]azulene-2-ylmethoxy)-propyl]-dimethyl-amine To a solution of 3-dimethylaminopropylchloride hydrochloride (2.37 g, 0.015 mole) in 50% sodium hydroxide (5 ml), benzyltriethylammonium chloride (0.25 g) and a toluene solution of alcohol 2 (0.2 g, 0.64 mmole) were added. The reaction mixture was heated under vigorous stirring and reflux for 3 hours. Then it was cooled to room temperature, diluted with water and extracted with dichloromethane. After purification by column chromatography an oily product (0.11 g) was isolated.

$^1$H NMR (ppm, CDCl$_3$): 1.93 (m, 2H); 2.39 (s, 6H); 2.59 (m, 2H); 3.64 (m, 2H); 4.72 (s, 2H); 7.05–7.56 (m, 8H).

Example 7

[2-(9-chloro-8-oxa-1-thia-dibenzo[e,h]azulene-2-ylmethoxy)-ethyl]-dimethyl-amine By the reaction of alcohol 2 (0.2 g, 0.64 mmole) and 2-dimethylaminoethylchloride hydrochloride (2.6 g, 0.015 mole), an oily product (0.15 g) was obtained.

$^1$H NMR (ppm, CDCl$_3$): 2.42 (s, 6H); 2.72 (m, 2H); 3.74 (m, 2H); 4.76 (s, 2H); 7.08–7.55 (m, 8H).

Example 8

4-[2-(9-chloro-8-oxa-1-thia-dibenzo[e,h]azulene-2-ylmethoxy)-ethyl]-morpholine

By the reaction of alcohol 2 (0.2 g, 0.64 mmole) and 4-(2-chloroethyl)-morpholine hydrochloride (2.8 g, 0.015 mole), an oily product (0.19 g) was obtained.

$^1$HNMR (ppm, CDCl$_3$): 2.51 (m, 4H); 3.71 (m, 8H); 4.75 (s, 2H); 7.08–7.56 (m, 8H).

Example 9

1-[2-(9-chloro-8-oxa-1-thia-dibenzo[e,h] azulene-2-ylmethoxy)-ethyl]-piperidine

By the reaction of alcohol 2 (0.2 g, 0.64 mmole) and 1-(2-chloroethyl)-piperidine monohydrochloride (2.76 g, 0.015 mmole), an oily product (0.13 g) was obtained.

Example 10

1-[2-(9-chloro-8-oxa-1-thia-dibenzo[e,h]azulene-2-ylmethoxy)-ethyl]-pyrrolidine

By the reaction of alcohol 2 (0.2 g, 0.64 mmole) and 1-(2-chloroethyl)-pyrrolidine hydrochloride (2.55 g, 0.015 mole), an oily product (0.15 g) was obtained.

$^1$H NMR (ppm, CDCl$_3$): 2.02 (m, 2H); 2.2 (m, 2H); 2.94 (m, 2H); 3.32 (m, 2H); 3.87 (m, 2H); 4.11 (m, 2H); 4.79 (s, 2H); 7.07–7.56 (m, 8H).

The compounds described in Examples 11–15 were prepared from alcohol 3 and the corresponding chloroalkyldialkyl-amine hydrochloride according to the process described in Example 11.

Example 11

[3-(11-chloro-8-oxa-1-thia-dibenzo[e,h]azulene-2-ylmethoxy)-propyl]-dimethyl-amine To a solution of 3-dimethylaminopropylchloride hydrochloride (2.2 g, 0.014 mole) in 50% sodium hydroxide (5 ml), benzyltriethylammonium chloride (0.25 g) and a toluene solution of alcohol 3 (0.19 g, 0.6 mmole) were added. The reaction mixture was heated under vigorous stirring and reflux for 5 hours. Then it was cooled to room temperature, diluted with water and extracted with dichloromethane. After purification by column chromatography an oily product (0.18 g) was isolated.

$^1$H NMR (ppm, CDCl$_3$): 2.05–2.14 (in, 2H); 2.63 (s, 6H); 2.91 (t, 2H); 3.71 (t, 2H); 4.74 (s, 2H); 7.2–7.5 (m, 8H).

Example 12

[2-(11-chloro-8-oxa-1-thia-dibenzo[e,h] azulene-2-ylmethoxy)-ethyl]-dimethyl-amine By the reaction of alcohol 3 (0.19 g, 0.6 mmole) and 2-dimethylaminoethylchloride hydrochloride (2.01 g, 0.014 mole), an oily product (0.2 g) was obtained.

$^1$H NMR(ppm, CDCl$_3$): 2.46 (s, 6H); 2.80 (t, 2H); 3.78 (t, 2H); 4.76 (s, 2H); 7.19–7.5 (m, 8H).

Example 13

4-[2-(11-chloro-8-oxa-1-thia-dibenzo[e,h]azulene-2-ylmethoxy)-ethyl]-morpholine

By the reaction of alcohol 3 (0.19 g, 0.6 mmole) and 4-(2-chloroethyl)-morpholine hydrochloride (2.8 g, 0.015 mole), an oily product (0.3 g) was obtained.

$^1$H NMR (ppm, CDCl$_3$): 2.61–2.84 (m, 6H); 3.82 (m, 6H); 4.77 (s, 2H); 7.2–7.48 (m, 8H).

Example 14

1-[2-(11-chloro-8-oxa-1-thia-dibenzo[e,h]azulene-2-ylmethoxy)-ethyl]-piperidine

By the reaction of alcohol 3 (0.19 g, 0.6 mmole) and 1-(2-chloroethyl)-piperidine monohydrochloride (2.76 g, 0.015 mole), an oily product (0.21 g) was obtained.

$^1$H NMR (ppm, CDCl$_3$): 1.43 (m, 2H); 1.85 (m, 2H); 2.25 (m, 2H); 2.75 (m, 2H); 3.14 (m, 2H); 3.65 (m, 2H); 4.01–4.15 (m, 2H); 4.84 (s, 2H); 7.15–7.65 (m, 8H).

Example 15

1-[2-(11-chloro-8-oxa-1-thia-dibenzo[e,h]azulene-2-ylmethoxy)-ethyl]-pyrrolidine By the reaction of alcohol 3 (0.19 g, 0.6 mmole) and 1-(2-chloroethyl)-pyrrolidine hydrochloride (2.55 g, 0.015 mole), an oily product (0.25 g) was obtained.

$^1$H NMR (ppm, CDCl$_3$): 1.8–2.2 (m, 8H); 2.9–3.25 (m, 2H); 3.98 (m, 2H); 4.8 (s, 2H); 7.19–7.45 (m, 8H).

The compounds described in Examples 16–20 were prepared from alcohol 4 and the corresponding chloroalkyl-dialkylamine hydrochloride according to the process described in Example 16.

Example 16
[3-(11-fluoro-8-oxa-1-thia-dibenzo[e,h]azulene-2-ylmethoxy)-propyl]-dimethylamine hydrochloride To a solution of 3-dimethylaminopropylchloride hydrochloride (2.2 g, 0.014 mole) in 50% sodium hydroxide (5 ml), benzyltriethylammonium chloride (0.15 g) and a toluene solution of alcohol 4 (0.2 g, 0.63 mmole) were added. The reaction mixture was heated under vigorous stirring and reflux for 4 hours. Then it was cooled to room temperature, diluted with water and extracted with dichloromethane. After purification by column chromatography an oily product (0.14 g) was isolated.

Example 17
[2-(11-fluoro-8-oxa-1-thia-dibenzo[e,h]azulene-2-ylmethoxy)-ethyl]-dimethyl-amine hydrochloride By the reaction of alcohol 4 (0.2 g, 0.63 mmole) and 2-dimethylaminoethylchloride hydrochloride (2.01 g, 0.014 mole), an oily product (0.24 g) was obtained, which was converted into the hydrochloride, m.p. 178–179° C.

C, H, N, S analysis: C, 61.53 (calc. 62.14); H, 5.19 (calc. 5.21); N, 3.72 (calc. 3.45); S 8.15 (calc. 7.90). $^1$H NMR (ppm, CDCl$_3$): 2.91 (d, 6H); 3.28 (m, 2H); 4.10 (m, 2H); 4.79 (s, 2H); 6.97–7.5 (m, 8H); 12.75 (s, 1H).

Example 18
4-[2-(11-fluoro-8-oxa-1-thia-dibenzo[e,h]azulene-2-ylmethoxy)-ethyl]-morpholine hydrochloride By the reaction of alcohol 4 (0.2 g, 0.63 mmole) and 4-(2-chloroethyl)-morpholine hydrochloride (2.6 g, 0.014 mole), an oily product (0.25 g) was obtained, which was converted into the hydrochloride, m.p. 207–208° C.

C, H, N, S analysis: C, 61.28 (calc. 61.67); H, 5.33 (calc. 5.18); N, 3.36 (calc. 3.13); S 7.44 (calc. 7.16). $^1$H NMR (ppm, CDCl$_3$): 3.05 (m, 2H); 3.25 (m, 2H); 3.57 (d, 2H); 3.97 (d, 2H); 4.19 (m, 2H); 4.35 (m, 2H); 4.79 (s, 2H); 7.0–7.47 (m, 8H).

Example 19
1-[2-(11-fluoro-8-oxa-1-thia-dibenzo[e,h]azulene-2-ylmethoxy)-ethyl]-piperidine hydrochloride By the reaction of alcohol 4 (0.2 g, 0.63 mmole) and 1-(2-chloroethyl)-piperidine monohydrochloride (2.6 g, 0.014 mole), an oily product (0.2 g) was obtained, which was converted into the hydrochloride, m.p. 122–124° C.

$^1$H NMR (ppm, CDCl$_3$): 1.95 (m, 4H); 2.17 (m, 2H); 2.27 (m, 2H); 2.75 (m, 2H); 3.12 (m, 2H); 3.65 (d, 2H); 4.78 (s, 2H); 6.98–7,68 (m, 8H); 12.2 (s, 1H).

Example 20
1-[2-(11-fluoro-8-oxa-1-thia-dibenzo[e,h]azulene-2-ylmethoxy)-ethyl]-pyrrolidine hydrochloride By the reaction of alcohol 4 (0.2 g, 0.63 mmole) and 1-(2-chloroethyl)-pyrrolidine hydrochloride (2.4 g, 0.014 mole), an oily product (0.27 g) was obtained, which was converted into the hydrochloride, m.p. 210° C.

C, H, N, S analysis: C, 63.02 (calc. 63.95); H, 5.42 (calc. 5.37); N, 3.48 (calc 3.24); S 7.62 (calc. 7.42). $^1$H NMR (ppm, CDCl$_3$): 2.09 (m, 2H); 2.17 (m, 2H); 2.94 (m, 2H); 3.31 (m, 2H); 3.85 (m, 2H); 4.10 (m, 2H); 4.79 (s, 2H); 6.97–7.48 (m, 8H); 12.3 (s, 1H).

The compounds described in Examples 21–25 were prepared from alcohol 5 and the corresponding chloroalkyl-dialkylamine hydrochloride according to the process described in Example 21.

Example 21
[3-(1,8-dithia-dibenzo[e,h]azulene-2-ylmethoxy)-propyl]-dimethylamine hydrochloride To a solution of 3-dimethylaminopropylchloride hydrochloride (2.2 g, 0.012 mole) in 50% sodium hydroxide (5 ml), benzyltriethylammonium chloride (0.15 g, 0.65 mmole) and a toluene solution of alcohol 5 (0.33 g, 0.0011 mole) were added. The reaction mixture was heated under vigorous stirring and reflux for 5 hours. Then it was cooled to room temperature, diluted with water and extracted with dichloromethane. After purification by column chromatography an oily product (0.32 g) was isolated. By the addition of concentrated hydrochloric acid into the cold ethanol solution of amine, a crystalline product was obtained.

C, H, N. S analysis: C, 62.74 (calc. 63.21); H, 5.83 (calc. 5.79); N, 3.63 (calc. 3.35); S 15.51 (calc. 15.34). $^1$H NMR (ppm, CDCl$_3$): 2.20 (in, 2H); 2.80 (d, 6H); 3.17 (m, 2H); 3.72 (m, 2H); 4.73 (s, 2H); 7.11–7.63 (m, 9H); 12.27 (s, 1H).

Example 22
[2-(1,8-dithia-dibenzo[e,h]azulene-2-ylmethoxy)-ethyl]-dimethyl-amine hydrochloride By the reaction of alcohol 5 (0.25 g, 0.84 mmole) and 2-dimethylaminoethylchloride hydrochloride (2.7 g, 0.019 mole), an oily product (0.22 g) was obtained, which was converted into the hydrochloride, m.p. 151° C.

$^1$H NMR (ppm, CDCl$_3$): 2.90 (m, 6H); 3.28 (m, 2H); 4.12 (m, 2H); 4.80 (s, 2H); 7.23–7.66 (m, 9H); 12.7 (s, 1H).

Example 23
4-[2-(1,8-dithia-dibenzo[e,h]azulene-2-ylmethoxy)-ethyl]-morpholine hydrochloride By the reaction of alcohol 5 (0.25 g, 0.84 mmole) and 4-(2-chloroethyl)-morpholine hydrochloride (3.47 g, 0.019 mole), an oily product (0.3 g) was obtained, which was converted into the hydrochloride, m.p. 178–183° C.

C, H, N, S analysis: C, 59.76 (calc. 61.93); H, 5.30 (calc. 5.42); N, 3.35 (calc. 3.14); S 13.89 (calc. 14.38). $^1$H NMR (ppm CDCl$_3$): 3.05 (m, 2H); 3.25 (m, 2H); 3.55 (m, 2H); 4.0 (m, 2H); 4.15–4.38 (m, 4H); 4.7 (s, 2H); 7.22–7.65 (m, 9H); 13.25 (s, 1H).

Example 24
1-[2-(1,8-dithia-dibenzo[e,h]azulene-2-ylmethoxy)-ethyl]-piperidine hydrochloride By the reaction of alcohol 5 (0.25 g, 0.84 mmole) and 1-(2-cliloroethyl)-piperidine monohydrochloride (3.3 g, 0.018 mole), an oily product (0.17 g) was obtained, which was converted into the hydrochloride, m.p. 173° C.

$^1$H NMR (ppm, CDCl$_3$): 1.46 (m, 2H); 1.95 (m, 4H), 2.27 (m, 2H); 2.85 (m, 2H); 3.32 (m, 2H); 3.68 (m, 2H); 4.12 (m, 2H); 7.22–7.35 (m, 9H); 10.97 (s, 1H).

Example 25
1-[2-(1,8-dithia-dibenzo[e,h]azulene-2-ylmethoxy)-ethyl]-pyrrolidine hydrochloride By the reaction of alcohol, 5 (0.25 g, 0.84 mmole) and 1-(2-chloroethyl)-pyrrolidine hydrochloride (3.1 g, 0.019 mole), an oily product (0.2 g) was obtained, which was converted into the hydrochloride.

The compounds described in Examples 26–30 were prepared from alcohol 6 and the corresponding chloroalkyl-dialkylamine hydrochloride according to the process described in Example 26.

Example 26
[3-(11-fluoro-1,8-dithia-dibenzo[e,h]azulene-2-ylmethoxy)-propyl]-dimethyl-amine hydrochloride To a solution of 3-dimethylaminopropylchloride hydrochloride (1.8 g, 0.011 mole) in 50% sodium hydroxide (5 ml), benzyltriethylammonium chloride (0.15 g) and a toluene solution of alcohol 6 (0.25 g, 0.8 mmole) were added. The reaction mixture was heated under vigorous stirring and reflux for 5 hours. Then it was cooled to room temperature, diluted with water and extracted with dichloromethane. After purification by column chromatography an oily product (0.18 g) was isolated. By the addition of concentrated hydrochloric acid into the cold ethanol solution of amine, a crystalline product was obtained, m.p. 209–214° C.

$^1$H NMR (ppm, CDCl$_3$): 2.30 (m, 2H); 2.88 (d, 6H); 3.24 (m, 2H); 3.80 (m, 2H); 4.82 (s, 2H); 7.08 (m, 1H); 7.28–7.71 (m, 7H); 12.5 (s, 1H).

Example 27
[2-(11-fluoro-1,8-dithia-dibenzo[e,h]azulene-2-ylmethoxy)-ethyl]-dimethyl-amine hydrochloride By the reaction of alcohol 6 (0.21 g, 0.67 mmole) and 2-dimethylaminoethylchloride hydrochloride (1.5 g, 0.01 mole), an oily product (0.22 g) was obtained, which was converted into the hydrochloride, m.p. 151–155° C.

$^1$H NMR (ppm, CDCl$_3$): 2.23 (s, 6H); 3.03 (m, 2H); 4.22 (m, 2H); 4.87 (s, 2H); 7.06–7.12 (m, 1H); 7.23–7.73 (m, 7H); 12.5 (s, 1H).

Example 28
4-[2-(11-fluoro-1,8-dithia-dibenzo[e,h]azulene-2-ylmethoxy)-ethyl]-morpholine hydrochloride By the reaction of alcohol 6 (0.21 g, 0.67 mmole) and 4-(2-chloroethyl)-morpholine hydrochloride (1.9 g, 0.01 mole), an oily product (0.15 g) was obtained, which was converted into the hydrochloride, m.p. 168–170° C.

$^1$H NMR (ppm, CDCl$_3$): 3.05 (m, 4H); 3.65 (m, 2H); 4.05 (m, 2H); 4.28 (m, 4H); 4.87 (s, 2H); 7.09 (m, 1H); 7.23–7.74 (m, 7H); 13.25 (s, 1H).

Example 29
1-[2-(11-fluoro-1,8-dithia-dibenzo[e,h]azulene-2-ylmethoxy)-ethyl]-piperidine hydrochloride By the reaction of alcohol 6 (0.21 g, 0.67 mmole) and 1-(2-chloroethyl)-piperidine monohydrochloride (1.9 g, 0.01 mole), an oily product (0.2 g) was obtained, which was converted into the hydrochloride, m.p. 214–216° C.

Example 30
1-[2-(11-fluoro-1,8-dithia-dibenzo[e,h]azulene-2-ylmethoxy)-ethyl]-pyrrolidine hydrochloride By the reaction of alcohol 6 (0.21 g, 0.67 mmole) and 1-(2-chloroethyl)-pyrrolidine hydrochloride (1.8 g, 0.01 mole), an oily product (0.17 g) was obtained, which was converted into the hydrochloride, m.p. 202–205° C.

$^1$H NMR (ppm, CDCl$_3$): 2.14 (m, 2H); 2.24 (m, 2H); 3.01 (m, 2H); 3.85 (m, 2H); 3.93 (m, 2H); 4.21 (m, 2H); 4.88 (s, 2H); 7.09 (m, 1H); 7.24–7.69 (m, 7H); 12.7 (s, 1H).

The compounds described in Examples 31–35 were prepared from alcohol 7 and the corresponding chloroalkyl-dialkylamine hydrochloride according to the process described in Example 31.

Example 31
[3-(11-chloro-1,8-dithia-dibenzo[e,h]azulene-2-ylmethoxy)-propyl]-dimethyl-amine hydrochloride To a solution of 3-dimethylaminopropylchloride hydrochloride (1.7 g, 0.011 mole) in 50% sodium hydroxide (5 ml), benzyltriethylammonium chloride (0.15 g) and al toluene solution of alcohol 7 (0.25 g, 0.75 mmole) were added. The reaction mixture was heated under vigorous stirring and reflux for 3 hours. Then it was cooled to room temperature, diluted with water and extracted with dichloromethane. After purification by column chromatography an oily product (0.17 g) was isolated, which was converted into the hydrochloride, m.p. 199–200° C.

$^1$H NMR (ppm, CDCl$_3$): 2.31 (m, 2H); 2.89 (d, 6H); 3.25 (m, 2H); 3.80 (m, 2H); 4.8 (s, 2H); 7.26–7.69 (m, 8H); 12.5 (s, 1H).

Example 32
[2-(11-chloro-1,8-dithia-dibenzo[e,h]azulene-2-ylmethoxy)-ethyl]-dimethyl-amine hydrochloride By the reaction of alcohol 7 (0.25 g, 0.75 mmole) and 2-dimethylaminoethylchloride hydrochloride (1.5 g, 0.011 mole), an oily product (0.2 g) was obtained, which was converted into the hydrochloride, m.p. 165–167° C.

$^1$H NMR (ppm, CDCl$_3$): 2.98 (s, 6H); 3.35 (m, 2H); 4.2 (m, 2H); 4.87 (s, 2H); 7.29–7.68 (m, 8H); 12.55 (s, 1H).

Example 33
4-[2-(11-chloro-1,8-dithia-dibenzo[e,h]azulene-2-ylmethoxy)-ethyl]-morpholine hydrochloride By the reaction of alcohol 7 (0.2 g, 0.61 mmole) and 4-(2-chloroethyl)-morpholine hydrochloride (1.9 g, 0.01 mole), an oily product (0.21 g) was obtained, which was converted into the hydrochloride, m.p. 190° C.

$^1$H NMR (ppm, CDCl$_3$): 3.08 (m, 2H); 3.32 (m, 2H); 3.63 (m, 2H); 4.05 (m, 2H); 4.25 (m, 4H); 4.87 (s, 2H); 7.29–7,69 (m, 8H); 13.25 (s, 1H).

Example 34
1-[2-(11-chloro-1,8-dithia-dibenzo[e,h]azulene-2-ylmethoxy)-ethyl]-piperidine hydrochloride By the reaction of alcohol 7 (0.2 g, 0.61 mmole) and 1-(2-chloroethyl)-piperidine monohydrochloride (1.9 g, 0.01 mole), an oily product (0.43 g) was obtained, which was converted into the hydrochloride, m.p. 184–185° C.

$^1$H NMR (ppm, CDCl$_3$): 1.51 (m, 3H); 2.23 (m, 7H); 3.07 (m, 2H); 3.18 (m, 2H); 4.23 (m, 2H); 7.32–7.74 (m, 8H); 12.3 (s, 1H).

Example 35
1-[2-(11-chloro-1,8-dithia-dibenzo[e,h]azulene-2-ylmethoxy)-ethyl]-pyrrolidine hydrochloride By the reaction of alcohol 7 (0.2 g, 0.61 mmole) and 1-(2-chloroethyl)-pyrrolidine hydrochloride (1.8 g, 0.01 mole), an oily product (0.27 g) was obtained, which was converted into the hydrochloride, m.p. 238° C.

$^1$H NMR (ppm, CDCl$_3$): 2.14 (m, 2H); 2.29 (m, 2H); 3.01 (m, 2H); 3.38 (m, 2H); 3.93 (m, 2H); 4.25 (m, 2H); 4.88 (s, 2H); 7.28–7.69 (m, 8H); 12.7 (s, 1H).

The compounds described in Examples 36–40 were prepared from alcohol 8 and the corresponding chloroalkyl-dialkylamine hydrochloride according to the process described in Example 36.

Example 36
[3-(11-bromo-1,8-dithia-dibenzo[e,h]azulene-2-ylmethoxy)-propyl]-dimethyl-amine hydrochloride To a solution of 3-dimethylaminopropylchloride hydrochloride (1.7 g, 0.011 mole) in 50% sodium hydroxide (5 ml), benzyltriethylammonium chloride (0.15 g) and a toluene solution of alcohol 8 (0.23 g, 0.61 mmole) were added. The reaction mixture was heated under vigorous stirring and reflux for 3 hours. Then it was cooled to room temperature,

Example 37
[2-(11-bromo-1,8-dithia-dibenzo[e,h]azulene-2-ylmethoxy)-ethyl]-dimethyl-amine hydrochloride By the reaction of alcohol 8 (0.23 g, 0.61 mmole) and 2-dimethylaminoethylchloride hydrochloride (1.5 g, 0.01 mole), an oily product (0.31 g) was obtained, which was converted into the hydrochloride, m.p. 147–150° C.

$^1$H NMR (ppm, CDCl$_3$): 2.22 (s, 6H); 2.97 (m, 2H); 4.22 (m, 2H); 4.86 (s, 2H); 7.28–7.72 (m, 8H); 12.25 (s, 1H).

Previous example (Example 36 continuation):
diluted with water and extracted with dichloromethane. After purification by column chromatography an oily product (0.25 g) was isolated, which was converted into the hydrochloride, m.p. 170–176° C.

$^1$H NMR (pppm, CDCl$_3$): 2.28 (m, 2H); 2.88 (d, 6H); 3.25 (m, 2H); 3.79 (m, 2H); 4.81 (s, 2H); 7.28–7.71 (m, 8H); 12.5 (s, 1H).

Example 38
4-[2-(11-bromo-1,8-dithia-dibenzo[e,h]azulene-2-ylmethoxy)-ethyl]-morpholine By the reaction of alcohol 8 (0.23 g, 0.61 mmole) and 4-(2-chloroethyl)-morpholine hydrochloride (2.2 g, 0.012 mole), an oily product (0.11 g) was obtained.

Example 39
1-[2-(11-bromo-1,8-dithia-dibenzo[e,h]azulene-2-ylmethoxy)-ethyl]-piperidine By the reaction of alcohol 8 (0.23 g, 0.61 mmole) and 1-(2-chloroethyl)-piperidine monohydrochloride (2.2 g, 0.012 mole), an oily product (0.09 g) was obtained.

Example 40
1-[2-(11-bromo-1,8-dithia-dibenzo[e,h]azulene-2-ylmethoxy)-ethyl]-pyrrolidine By the reaction of alcohol 8 (0.23 g, 0.61 mmole) and 1-(2-chloroethyl)-pyrrolidine hydrochloride (2.2 g, 0.012 mole), an oily product (0.17 g) was obtained.

$^1$H NNM (ppm, CDCl$_3$): 2.02 (m, 4H); 3.05 (m, 6H); 3.96 (m, 2H); 4.81 (s, 2H), 7.23–7.76 (m, 8H).

The compounds described in Examples 41–45 were prepared from alcohol 9 and the corresponding chloroalkyl-dialkylamine hydrochloride according to the process described in Example 41.

Example 41
[3-(10-trifluoromethyl-1,8-dithia-dibenzo[e,h]azulene-2-ylmethoxy)-propyl]-dimethyl-amine To a solution of 3-dimethylaminopropylchloride hydrochloride (1.1 g, 0.007 mole) in 50% sodium hydroxide (5 ml), benzyltriethylammonium chloride (0.15 g) and a toluene solution of alcohol 9 (0.18 g, 0.5 mmole) were added. The reaction mixture was heated under vigorous stirring and reflux for 3 hours. Then it was cooled to room temperature, diluted with water and extracted with dichloromethane. After purification by column chromatography an oily product (0.11 g) was isolated.

$^1$H NMR (ppm, CDCl$_3$): 2.21 (m, 2H); 2.48 (s, 6H); 2.71 (m, 2H); 3.69 (t, 2H); 4.76 (s, 2H), 7.23–7.89 (m, 8H).

Example 42
Dimethyl-[2-(10-trifluoromethyl-1,8-dithia-dibenzo[e,h]azulene-2-ylmethoxy)-ethyl]-amine hydrochloride By the reaction of alcohol 9 (0.18 g, 0.5 mmole) and 2-dimethylaminoethylchloride hydrochloride (1 g, 0.007 mole), an oily product was obtained, which was converted into the hydrochloride (0.1 g).

$^1$H NMR (ppm, CDCl$_3$): 2.94 (s, 6H); 3.32 (m, 2H); 4.18 (m, 2H); 4.85 (s, 2H); 7.29–7.70 (m, 7H); 7.93 (s, 1H); 12.85 (s, 1H).

Example 43
4-[2-(10-trifluoromethyl-1,8-dithia-dibenzo[e,h]azulene-2-ylmethoxy)-ethyl]-morpholine By the reaction of alcohol 9 (0.18 g, 0.5 mmole) and 4-(2-chloroethyl)-morpholine hydrochloride (1.3 g, 0.007 mole), an oily product (0.20 g) w as obtained.

$^1$H NMR (ppm, CDCl$_3$): 2.55 (m, 7H); 3.58 (m, 2H); 3.74 (m, 3H); 4.79 (s, 2H); 7.24–7.90 (m, 8H).

Example 44
1-[2-(10-trifluoromethyl-1,8-dithia-dibenzo[e,h]azulene-2-ylmethoxy)-ethyl]-piperidin hydrochloride By the reaction of alcohol 9 (0.18 g, 0.5 mmole) and 1-(2-chloroethyl)-piperidine monohydrochloride (1.3 g, 0.007 mole), an oily product (0.18 g) was obtained, which was converted into the hydrochloride.

$^1$HNMR (ppm, CDCl$_3$): 1.85 (m, 2H); 2.75–3.17 (m, 6H); 3.23 (m, 2H); 3.88 (m, 4H); 4.81 (s, 2H); 7.25–7.90 (m, 8H); 12.3 (s, 1H).

Example 45
1-[2-(10-trifluoromethyl-1,8-dithia-dibenzo[e,h]azulene-2-ylmethoxy)-ethyl]-pyrrolidine hydrochloride By the reaction of alcohol 9 (0.18 g, 0.5 mmole) and 1-(2-chloroethyl)-pyrrolidine hydrochloride (1.2 g, 0.007 mole), an oily product (0.1 g) was obtained, which was converted into the hydrochloride.

$^1$H NMR (ppm, CDCl$_3$): 2.01 (m, 2H); 2.75 (m, 2H); 3.10 (m, 4H); 3.99 (m, 2H), 4.17 (m, 2H); 4.83 (s, 2H); 7.26–7.91 (m, 8H); 12.3 (s, 1H).

The compounds described in Examples 46–49 were prepared from alcohol 10 and the corresponding chloroalkyl-dialkylamine hydrochloride according to the process described in Example 46.

Example 46
[3-(10-chloro-1,8-dithia-dibenzo[e,h]azulene-2-ylmethoxy)-propyl]-dimethyl-amine To a solution of 3-dimethylaminopropylchloride hydrochloride (1.1 g, 0.007 mole) in 50% sodium hydroxide (5 ml), benzyltriethylammonium chloride (0.15 g) and a toluene solution of alcohol 10 (0.16 g, 0.48 mmole) were added. The reaction mixture was heated under vigorous stirring and reflux for 3 hours. Then it was cooled to room temperature, diluted with water and extracted with dichloromethane. After purification by column chromatography an oily product (0.17 g) was isolated.

$^1$H NMR (ppm, CDCl$_3$): 1.91 (m, 2H); 2.36 (s, 6H); 2.56 (m, 2H), 3.69 (t, 2H); 4.74 (s, 2H); 7.2–7.7 (m, 8H).

Example 47
[2-(10-chloro-1,8-dithia-dibenzo[e,h]azulene-2-ylmethoxy)-ethyl]-dimethyl-amine hydrochloride By the reaction of alcohol 10 (0.16 g, 0.48 mmole) and 2-dimethylaminoethylchloride hydrochloride (0.98 g, 0.0068 mole), an oily product was obtained, which was converted into the hydrochloride (0.12 g).

$^1$H NMR (ppm, CDCl$_3$): 2.36 (s, 6H); 2.65 (m, 2H); 3.73 (m, 2H); 4.78 (s, 2H); 7.2–7.7 (m, 8H); 7.93 (s, 1H).

Example 48
1-[2-(10-chloro-1,8-dithia-dibenzo[e,h]azulene-2-ylmethoxy)-ethyl]-piperidine hydrochloride By the reaction of alcohol 10 (0.16 g, 0.48 mmole) and 1-(2-chloroethyl)-piperidine monohydrochloride (1.25 g, 0.0067 mole), an oily product (0.11 g) was obtained, which was converted into the hydrochloride.

$^1$H NMR (ppm, CDCl$_3$): 1.57 (m, 2H); 2.95–3.87 (m, 10H); 4.78 (s, 2H); 7.2–7. (m, 8H).

Example 49
1-[2-(10-chloro-1,8-dithia-dibenzo[e,h]azulene-2-ylmethoxy)-ethyl]-pyrrolidine By the reaction of alcohol 10 (0.16 g, 0.48 mmole) and 1-(2-chloroethyl)-pyrrolidine hydrochloride (1.15 g, 0.0067 mole), an oily product (0.14 g) was obtained.

$^1$H NMR (ppm, CDCl$_3$): 1.87 (m, 4H); 2.76 (m, 4H); 2.88 (m, 2H); 3.86 (m, 2H); 4.78 (s, 2H); 7.2–7.65 (m, 8H).

The compounds described in Examples 50–54 were prepared from alcohol 11 and the corresponding chloroalkyl-dialkylamine hydrochloride according to the process described in Example 50.

Example 50
[3-(10-bromo-1,8-dithia-dibenzo[e,h]azulene-2-ylmethoxy)-propyl]-dimethyl-amine hydrochloride To a solution of 3-dimethylaminopropylchloride hydrochloride (1.18 g, 0.0074 mole) in 50% sodium hydroxide (5 ml), benzyltriethylammonium chloride (0.15 g) and a toluene solution of alcohol 11 (0.2 g, 0.53 mmole) were added. The reaction mixture was heated wider vigorous stirring and reflux for 3 hours. Then it was cooled to room temperature, diluted with water and extracted with dichloromethane. After purification by column chromatography an oily product (0.17 g) was isolated, which was converted into the hydrochloride.

$^1$HNMR (ppm, CDCl$_3$): 2.23 (m, 2H); 2.81 (d, 6H); 3.17 (m, 2H; 3.74 (m, 2H), 4.75 (s, 2H); 7.21–7.81 (m, 8H); 12.3 (s, 1H).

Example 51
[2-(10-bromo-1,8-dithia-dibenzo[e,h]azulene-2-ylmethoxy)-ethyl]-dimethyl-amine hydrochloride By the reaction of alcohol 11 (0.2 g, 0.53 mmole) and 2-dimethylaminoethylchloride hydrochloride (1.18 g, 0.0074 mole), an oily product was obtained, which was converted into the hydrochloride (0.12 g).

$^1$H NMR (ppm, CDCl$_3$): 2.91 (m, 6H); 3.27 (m, 2H); 4.15 (m, 2H); 4.80 (s, 2H); 7.23–7.84 (m, 8H); 12.4 (s, 1H).

Example 52
1-[2-(10-bromo-1,8-dithia-dibenzo[e,h]azulene-2-ylmethoxy)-ethyl]-piperidine hydrochloride By the reaction of alcohol 11 (0.2 g, 0.53 mmole) and 1-(2-chloroethyl)-piperidine monohydrochloride (1.27 g, 0.0074 mole), an oily product (0.15 g) was obtained, which was converted into the hydrochloride.

$^1$H NMR (CDCl$_3$): 1.38 (m, 2H); 1.85 (m, 2H); 2.17–2.36 (m, 2H); 2.76 (m, 2H); 3.12 (m, 2H); 3.17 (m, 2H); 4.18 (m, 2H); 4.78 (s, 2H); 7.25–7.90 (m, 8H); 12.3 (s, 1H).

Example 53
1-[2-(10-bromo-1,8-dithia-dibenzo[e,h]azulene-2-ylmethoxy)-ethyl]-pyrrolidine By the reaction of alcohol 11 (0.2 g, 0.53 mmole) and 1-(2-chloroethyl)-pyrrolidine hydrochloride (1.37 g, 0.0074 mole), an oily product (0.09 g) was obtained.

$^1$H NMR (CDCl$_3$): 1.69 (m, 4H); 2.62 (m, 4H); 2.69 (m, 2H); 3.81 (m, 2H); 4.78 (s, 2H); 7.22–7.85 (m, 8H).

Example 54
[2-(10-bromo-1,8-dithia-dibenzo[e,h]azulene-2-ylmethoxy)-propyl]-dimethyl-amine hydrochloride By the reaction of alcohol 11 (0.2 g, 0.53 mmole) and 1-dimethylamino-2-propylchloride hydrochloride (1.18 g, 0.0074 mole), an oily product (0.12 g) was obtained, which was converted into the hydrochloride.

$^1$H NMR (ppm, CDCl$_3$): 1.17 (d, 3H); 2.47 (s, 6H); 3.02 (m, 1H); 3.68 (m, 2H); 4.77 (s, 2H); 7.1–7.85 (m, 8H).

The compounds described in Examples 55–57 were prepared from alcohol 12 and the corresponding chloroalkyl-dialkylamine hydrochloride according to the process described in Example 55.

Example 55
[3-(9,11-dimethyl-1,8-dithia-dibenzo[e,h]azulene-2-ylmethoxy)-propyl]-dimethyl-amine hydrochloride To a solution of 3-dimethylaminopropylchloride hydrochloride (1.23 g, 0.0077 mole) in 50% sodium hydroxide (5 ml), benzyltriethylammonium chloride (0.15 g) and a toluene solution of alcohol 12 (0.18 g, 0.55 mmole) were added. The reaction mixture was heated under vigorous stirring and reflux for 3 hours. Then it was cooled to room temperature, diluted with water and extracted with dichloromethane. After purification by column chromatography an oily product (0.13 g) was isolated, which was converted into the hydrochloride.

$^1$H NMR (ppm, CDCl$_3$): 2.22 (m, 2H); 2.29 (s, 3H); 2.61 (s, 3H); 2.81 (s, 6H); 3.17 (m, 2H); 3.74 (m, 2H); 4.75 (s, 2H); 7.11–7.67 (m, 7H); 12.3 (s, 1H).

Example 56
[2-(9,11-dimethyl-1,8-dithia-dibenzo[e,h]azulene-2-ylmethoxy)-ethyl]-dimethyl-amine hydrochloride By the reaction of alcohol 12 (0.18 g, 0.55 mmole) and 2-dimethylaminoethylchloride hydrochloride (1.12 g, 0.0077 mole), an oily product was obtained, which was converted into the hydrochloride (0.09 g).

$^1$H NMR (ppm, CDCl$_3$): 2.29 (s, 3H); 2.61 (s, 3H); 2.91 (m, 6H); 3.28 (m, 2H); 4.13 (m, 2H); 4.80 (s, 2H); 7.12–7.67 (m, 7H); 12.3 (s, 1H).

Example 57
1-[2-(9,11-dimethyl-1,8-dithia-dibenzo[e,h]azulene-2-ylmethoxy)-ethyl]-pyrrolidine hydrochloride By the reaction of alcohol 12 (0.18 g, 0.55 mmole) and 1-(2-chloroethyl)pyrrolidine hydrochloride (1.32 g, 0.0077 mole), an oily product (0.11 g) was obtained.

$^1$H NMR (ppm, CDCl$_3$): 2.07 (m, 2H); 2.24 (m, 2H); 2.69 (m, 2H); 2.29 (s, 3H), 2.61 (s, 3H); 2.95 (m, 2H); 3.31 (m, 2H); 3.85 (m, 2H); 4.12 (m, 2H); 4.80 (s, 2H); 7.22–7.85 (m, 7H); 12.5 (s, 2H).

The compounds described in Examples 58–62 were prepared from alcohol 13 and the corresponding chloroalkyl-dialkylamine hydrochloride according to the process described in Example 58.

Example 58
[3-(10,11-dichloro-1,8-dithia-dibenzo[e,h]azulene-2-ylmethoxy)-propyl]-dimethyl-amine hydrochloride To a solution of 3-dimethylaminopropylchloride hydrochloride (1.5 g, 0.0095 mole) in 50% sodium hydroxide (5 ml), benzyltriethylammonium chloride (0.15 g) and a toluene solution of alcohol 13 (0.2 g, 0.68 mmole) were added. The reaction mixture was heated under vigorous stirring and reflux for 3 hours. Then it was cooled to room temperature, diluted with water and extracted with dichloromethane. After purification by column chromatography an oily product was isolated, which was converted into the hydrochloride (0.075 g).

$^1$H NMR (ppm, CDCl$_3$): 2.25 (m, 2H); 2.83 (s, 6H); 3.19 (m, 2H); 3.75 (m, 2H); 4.76 (s, 2H); 7.22–7.74 (m, 7H); 12.35 (s, 1H).

Example 59
[2-(10,11-dichloro-1,8-dithia-dibenzo[e,h]azulene-2-ylmethoxy)-ethyl]-dimethyl-amine hydrochloride By the reaction of alcohol 13 (0.2 g, 0.68 mmole) and 2-dimethylaminoethylchloride hydrochloride (1.4 g, 0.0095 mole), an oily product was obtained, which was converted into the hydrochloride (0.08 g).

$^1$N NMR (ppm, CDCl$_3$): 2.97 (s, 6H); 3.47 (m, 2H); 4.15 (m, 2H); 4.81 (s, 2H); 7.23–7.74 (m, 7H); 12.3 (s, 1H).

Example 60
4-[2-(10,11-dichloro-1,8-dithia-dibenzo[e,h]azulene-2-ylmethoxy)-ethyl]-morpholine hydrochloride By the reaction of alcohol 13 (0.2 g, 0.68 mmole) and 4-(2-chloroethyl)-morpholine hydrochloride (1.7 g, 0.0095 mole), an oily product was obtained, which was converted into the hydrochloride (0.11 g).

$^1$H NMR (ppm, CDCl$_3$): 3.02 (m, 2H); 3.27 (m, 2H); 3.60 (m, 2H); 3.99 (m, 2H); 4.16–4.36 (m, 4H); 4.80 (s, 2H); 7.22–7.74 (m, 7H); 12.55 (s, 1H).

Example 61
1-[2-(10,11-dichloro-1,8-dithia-dibenzo[e,h]azulene-2-ylmethoxy)-ethyl]-piperidine hydrochloride By the reaction of alcohol 13 (0.2 g, 0.68 mmole) and 1-(2-chloroethyl)-piperidine monohydrochloride (1.7 g, 0.0095 mole), an oily product was obtained, which was converted into the hydrochloride (0.045 g).

$^1$H NMR (ppm, CDCl$_3$): 1.42 (m, 2H); 1.87 (m, 2H); 2.23–2.37 (m, 2H); 2.78 (m, 2H); 3.22 (m, 2H); 3.65 (m, 2H); 4.19 (m, 2H); 4.79 (s, 2H); 7.22–7.74 (m, 7H); 12.1 (s, 1H).

Example 62
1-[2-(10,11-dichloro-1,8-dithia-dibenzo [e,h]azulene-2-ylmethoxy)-ethyl]-pyrrolidine hydrochloride By the reaction of alcohol 13 (0.2 g, 0.68 mmole) and 1-(2-chloroethyl)-pyrrolidine hydrochloride (1.62 g, 0.0095 mole), an oily product was obtained, which was converted into the hydrochloride (0.09 g).

$^1$H NMR (ppm, CDCl$_3$): 2.02–2.25 (m, 4H); 2.94 (m, 2H); 3.32 (m, 2H); 3.88 (m, 2H); 4.15 (m, 2H); 4.81 (s, 2H); 7.22–7.73 (m, 7H); 12.4 (s, 1H).

The compounds described in Examples 63–64 were prepared from alcohol 14 and the corresponding chloroalkyl-dialkylamine hydrochloride according to the process described in Example 63.

Example 63
[3-(9-chloro-11-fluoro-1,8-dithia-dibenzo[e,h]azulene-2-ylmethoxy)-propyl]-dimethyl-amine hydrochloride To a solution of 3-dimethylaminopropylchloride hydrochloride (1.22 g, 0.0077 mole) in 50% sodium hydroxide (5 ml), benzyltriethylammonium chloride (0.15 g) and a toluene solution of alcohol 14 (0.19 g, 0.55 mmole) were added. The reaction mixture was heated under vigorous stirring and reflux for 3 hours. Then it was cooled to room temperature, diluted with water and extracted with dichloromethane. After purification by column chromatography an oily product was isolated, which was converted into the hydrochloride (0.095 g).

$^1$H NMR (ppm, CDCl$_3$): 2.24 (m, 2H); 2.82 (s, 6H); 3.18 (m, 2H); 3.74 (m, 2H); 4.77 (s, 2H); 7.11–7.73 (m, 7H); 12.35 (s, 1H).

Example 64
[2-(9-chloro-11-fluoro-1,8-dithia-dibenzo[e,h]azulene-2-ylmethoxy)-ethyl]-dimethyl-amine hydrochloride By the reaction of alcohol 14 (0.19 g, 0.55 mmole) and 2-dimethylaminoethylchloride hydrochloride (1.12 g, 0.0077 mole), an oily product was obtained, which was converted into the hydrochloride (0.07 g).

$^1$H NMR (ppm, CDCl$_3$): 2.97 (m, 6H); 3.37 (m, 2H), 4.2 (m, 2H); 4.87 (s, 2H); 7.08–7.79 (m, 7H); 12.5 (s, 1H).

Example 65
3-(11-chloro-8-oxa-1-thia-dibenzo[e,h]azulene-2-ylmethoxy)-propylamine To a solution of 3-chloropropylamine hydrochloride (1.03 g, 7.96 mmole) in 50% sodium hydroxide (10 ml), benzyl-triethylammonium chloride (0.3 g) and a toluene solution of alcohol 3 (0.25 g, 0.79 mmole) were added. The reaction mixture was heated under vigorous stirring and reflux for 3 hours. Then it was cooled to room temperature, diluted with water and extracted with dichloromethane. After purification by column chromatography, an oily product was isolated.

$^1$H NMR (ppm, CDCl$_3$): 1.91 (m, 2H); 2.99 (t, 2H); 3.67 (t, 2H); 4.73 (s, 2H); 7.15–7.45 (m, 8H).

MS (m/z): 372.1 (MH$^+$).

Example 66
3-(8-oxa-1-thia-dibenzo[e,h]azulene-2-ylmethoxy)-propylamine

The compound was prepared as described in Example 65 by the reaction of alcohol 1 (0.3 g, 1.1 mmole) and 3-chloropropylamine-hydrochloride (1.4 g, 0.011 mole), whereat an oily product was obtained.

$^1$H NMR (ppm, CDCl$_3$): 2.02 (m, 2H); 3.14 (t, 2H); 3.66 (t, 2H); 4.72 (s, 2H); 7.15–7.45 (m, 9H).

MS (m/z): 338.2 (MH$^+$).

Example 67
N,N-dimethyl-[3-(11-methylsulfanyl-1,8-dithia-dibenzo[e,h]azulene-2-ylmethoxy)-propyl]-amine To a solution of 3-dimethylaminopropylchloride-hydrochloride (1.3 g, 0.0082 mole) in 50% sodium hydroxide (6 ml), benzyltriethylammonium chloride (0.18 g, 0.79 mmole) and a toluene solution of alcohol 20 (0.2 g, 0.58 mmole) were added. The reaction mixture was heated under vigorous stirring and reflux for 4 hours. Then it was cooled to room temperature, diluted with water and extracted with dichloromethane. After purification by column chromatography, an oily product was isolated (0.11 g).

$^1$H NMR (ppm, CDCl$_3$): 2.03 (m, 2H); 2.48 (s, 3H); 2.53 (s, 6H); 2.79 (t, 2H); 3.69 (t, 2H); 4.74 (s, 2H); 7.15–7.65 (m, 8H).

Example 68
N,N-dimethyl-[2-(11-methylsulfanyl-1,8-dithia-dibenzo[e,h]azulene-2-ylmethoxy)-ethyl]-amine The compound was prepared as described in Example 67 by the reaction of alcohol 20 (0.2 g, 0.58 mmole) and 2-dimethylaminoethylchloride-hydrochloride (1.2 g, 8.2 mmole), whereat an oily product was obtained (0.13 g).

$^1$H NMR (ppm, CDCl$_3$): 2.45 (s, 3H); 2.47 (s, 6H); 2.77 (t, 2H); 3.81 (m, 2H); 4.77 (s, 2H); 7.2–7.6 (m, 8H).

Example 69
N,N-dimethyl-[3-(10-methyl-1,8-dithia-dibenzo[e,h]azulene-2-ylmethoxy)-propyl]-amine To a solution of 3-dimethylaminopropylchloride-hydrochloride (1.4 g, 8.8 mmole) in 50% sodium hydroxide (7 ml), benzyltriethylammonium chloride (0.2 g, 0.88 mmole) and a toluene solution of alcohol 21 (0.25 g, 0.63 mmole) were added. The reaction mixture was heated under vigorous stirring and reflux for 4 hours. Then it was cooled to room temperature, diluted with water and extracted with dichloromethane. After purification by column chromatography, an oily product was isolated.

$^1$H NMR (ppm, CDCl$_3$): 2.01 (m, 2H); 2.34 (s, 3H); 2.53 (s, 6H); 2.82 (s, 2H); 3.68 (t, 2H); 4.73 (s, 2H); 7.15–7.65 (m, 8H).

MS (m/z): 396 (MH$^+$).

Example 70
N,N-dimethyl-[2-(10-methyl-1,8-dithia-dibenzo[e,h]azulene-2-ylmethoxy)-ethyl]-amine The compound was prepared as described in Example 69 by the reaction of alcohol 21 (0.25 g, 0.63 mmole) and 2-dimethylaminoethylchloride-hydrochloride (1.28 g, 8.8 mmole), whereat an oily product was obtained (0.2 g).

$^1$H NMR (ppm, CDCl$_3$): 2.34 (s, 3H); 2.43 (s, 6H); 2.73 (t, 2H); 3.77 (t, 2H); 4.78 (s, 2H); 7.1–7.6 (m, 8H).

Example 71
N,N-dimethyl-[3-(11-methyl-1,8-dithia-dibenzo[e,h]azulene-2-ylmethoxy)-propyl]-amine To a solution of 3-dimethylaminopropylchloride-hydrochloride (1.4 g, 8.8 mmole) in 50% sodium hydroxide (10 ml), benzyltriethylammonium chloride (0.2 g, 0.88 mmole) and a toluene solution of alcohol 22 (0.25 g, 0.63 mmole) were added. The reaction mixture was heated under vigorous stirring and reflux for 4 hours. Then it was cooled to room temperature, diluted with water and extracted with dichloromethane. After purification by column chromatography, an oily product was isolated (0.21 g).

$^1$H NMR (ppm, CDCl$_3$): 1.91 (m, 2H); 2.34 (s, 6H); 2.38 (s, 3H); 2.53 (t, 2H); 3.69 (t, 2H); 4.77 (s, 2H); 7.15–7.67 (m, 8H).

Example 72
N,N-dimethyl-[2-(11-methyl-1,8-dithia-dibenzo[e,h]azulene-2-ylmethoxy)-ethyl]-amine The compound was prepared as described in Example 71 by the reaction of alcohol 22 (0.25 g, 0.63 mmole) and 2-dimethylaminoethylchloride-hydrochloride (1.3 g, 8.8 mmole), whereat an oily product was obtained (0.2 g).

$^1$H NMR (ppm, CDCl$_3$): 2.34 (s, 3H); 2.56 (s, 6H); 2.87 (m, 2H); 3.87 (m, 2H); 4.78 (s, 2H); 7.1–7.6 (m, 8H).

Example 73
N,N-dimethyl-[3-(10-methoxy-8-oxa-1-thia-dibenzo[e,h]azulene-2-ylmethoxy)-propyl]-amine To a solution of 3-dimethylaminopropylchloride-hydrochloride (0.75 g, 4.17 mmole) in 50% sodium hydroxide (10 ml), benzyltriethylammonium chloride (0.1 g, 0.44 mmole) and a toluene solution of alcohol 23 (0.2 g, 0.64 mmole) were added. The reaction mixture was heated under vigorous stirring and reflux for 4 hours. Then it was cooled to room temperature, diluted with water and extracted with dichloromethane. After purification by column chromatography an oily product was isolated (0.075 g).

$^1$H NMR (ppm, CDCl$_3$): 1.94 (m, 2H); 2.39 (s, 6H); 2.82 (m, 2H); 3.63 (t, 2H); 3.83 (s, 3H); 4.7 (s, 2H); 6.7–7.46 (m, 8H).

MS (m/z): 396 (MH$^+$)

Example 74
N,N-dimethyl-[2-(10-methoxy-8-oxa-1-thia-dibenzo[e,h]azulene-2-ylmethoxy)-ethyl]-amine The compound was prepared as described in Example 73 by the reaction of alcohol 23 (0.2 g, 0.64 mmole) and 2-dimethylaminoethylchloride-hydrochloride (0.75 g, 5.15 mmole), whereat an oily product was obtained (0.063 g).

$^1$H NMR (ppm, CDCl$_3$): 2.65 (s, 6H); 2.99 (m, 2H); 3.84 (s, 3H); 3.91 (m, 2H); 4.76 (s, 2H); 6.73–7.4 (m, 8H).

MS (m/z): 382 (MH$^+$)

Example 75
1-[2-(10-methoxy-8-oxa-1-thia-dibenzo[e,h]azulene-2-ylmethoxy)-ethyl]-piperidine The compound was prepared as described in Example 73 by the reaction of alcohol 23 (0.2 g, 0.64 mmole) and 1-(2-chloroethyl)piperidine-hydrochloride (0.75 g, 4.1 mmole), whereat an oily product was obtained (0.04 g).

MS (m/z): 421 (MH$^+$)

Example 76
1-[2-(10-methoxy-8-oxa-1-thia-dibenzo[e,h]azulene-2-ylmethoxy)-ethyl]-pyrrolidine The compound was prepared as described in Example 73 by the reaction of alcohol 23 (0.2 g, 0.64 mmole) and 1-(2-chloroethyl)pyrrolidine-hydrochloride (0.75 g, 4.4 mmole), whereat an oily product was obtained (0.050 g).

MS (m/z): 408 (MH$^+$)

Example 77
3-(10-methoxy-8-oxa-1-thia-dibenzo[e,h]azulene-2-ylmethoxy)-propylamine The compound was prepared as described in Example 73 by the reaction of alcohol 23 (0.2 g, 0.64 mmole) and 3-chloropropamine-hydrochloride (0.75 g, 5.7 mmole), whereat an oily product was obtained (0.04 g).

MS (m/z): 368.2 (MH$^+$)

Example 78
N,N-dimethyl-[3-(6-chloro-1,8-dithia-dibenzo[e,h]azulene-2-ylmethoxy)-propyl]-amine To a solution of 3-dimethylaminopropylchloride-hydrochloride (0.48 g, 3.0 mmole) in 50% sodium hydroxide (5 ml), benzyltriethylammonium chloride (0.2 g, 0.88 mmole) and a toluene solution of alcohol 24 (0.1 g, 0.3 mmole) were added. The reaction mixture was heated under vigorous stirring and reflux for 4 hours. Then it was cooled to room temperature, diluted with water and extracted with dichloromethane. After purification by column chromatography an oily product was isolated (0.09 g).

$^1$H NMR (ppm, CDCl$_3$): 1.91 (m, 2H); 2.35 (s, 6H); 2.55 (t, 2H); 3.66 (t, 2H); 4.73 (s, 2H); 7.16–7.64 (m, 8H).

MS (m/z): 416 (MH$^+$)

Example 79
N,N-dimethyl-[2-(6-chloro-1,8-dithia-dibenzo[e,h]azulene-2-ylmethoxy)-ethyl]-amine The compound was prepared as described in Example 78 by the reaction of alcohol 24 (0.15 g, 0.63 mmole) and 2-dimethylaminoethylchloride-hydrochloride (0.65 g, 4.5 mmole), whereat an oily product was obtained (0.08 g).

$^1$H NMR (ppm, CDCl$_3$): 2.56 (s, 6H); 2.89 (t, 2H); 3.88 (t, 2H); 4.78 (s, 2H); 7.2–7.6 (m, 8H).

MS (m/z): 402 (MH$^+$)

Example 80
3-[6-chloro-1,8-dithia-dibenzo[e,h]azulene-2-ylmethoxy)-propyl]-amine The compound was prepared as described in Example 27 by the reaction of alcohol 24 (0.15 g, 0.45 mmole) and 3-chloropropylamine-hydrochloride (0.59 g, 4.5 mmole), whereat an oily product was obtained (0.1 g).

MS (m/z): 388.1 (MH$^+$)

Example 81
N,N-dimethyl-[3-(10-fluoro-1,8-dithia-dibenzo[e,h]azulene-2-ylmethoxy)-propyl]-amine To a solution of 3-dimethylaminopropylchloride-hydrochloride (1.41 g, 8.9 mmole) in 50% sodium hydroxide (7 ml), benzyltriethylammonium chloride (0.2 g, 0.88 mmole) and a toluene solution of alcohol 27 (0.2 g, 0.64 mmole) were added. The reaction mixture was heated under vigorous stirring and reflux for 4 hours. Then it was cooled to room temperature, diluted with water and extracted with dichloromethane. After purification by column chromatography an oily product was isolated (0.097 g).

$^1$H NMR (ppm, CDCl$_3$): 1.9 (m, 2H); 2.37 (s, 6H); 2.58 (m, 2H); 3.67 (t, 2H); 4.73 (s, 2H); 7.0–7.65 (m, 8H).

Example 82
N,N-dimethyl-[2-(10-fluoro-1,8-dithia-dibenzo[e,h]azulene-2-ylmethoxy)-ethyl]-amine The compound was prepared as described in Example 81 by the reaction of alcohol 27 (0.2 g, 0.64 mmole) and 2-dimethylaminoethylchloride-hydrochloride (1.28 g, 8.9 mmole), whereat an oily product was obtained (0.085 g).

$^1$H NMR (ppm, CDCl$_3$): 2.46 (s, 6H); 2.79 (t, 2H); 3.79 (t, 2H); 4.76 (s, 2H); 7.0–7.63 (m, 8H).

Example 83
[2-(3-dimethylamino-propoxymethyl)-1-thia-8-aza-dibenzo[e,h]azulene-8-yl]-phenyl-methanon The compound was prepared as described in Example 81 by the reaction of alcohol 25 (0.15 g, 0.39 mmole) and 3-dimethylaminopropylchloride-hydrochloride (0.62 g, 3.9 mmole), whereat an oily product was obtained (0.03 g).

$^1$H NMR (ppm, CDCl$_3$): 1.96 (p, 2H); 2.38 (s, 6H); 2.60 (t, 2H); 3.70 (t, 2H); 4.79 (s, 2H); 7.10–7.60 (m, 14H).

Example 84
[2-(2-dimethylamino-ethoxymethyl)-1-thia-8-aza-dibenzo[e,h]azulene-8-yl]-phenyl-methanon The compound was prepared as described in Example 81 by the reaction of alcohol 25 (0.15 g, 0.39 mmole) and 2-dimethylaminoethylchloride-hydrochloride (0.56 g, 3.9 mmole), whereat an oily product was obtained (0.04 g).

$^1$H NMR (ppm, DMSO): 2.17 (s, 6H); 2.45 (t, 2H); 3.58 (t, 2H); 4.65 (s, 2H); 6.90–7.63 (m, 14H).

Example 85
N,N-dimethyl-[3-(8H-1-thia-8-aza-dibenzo[e,h]azulene-2-ylmethoxy)-propyl]-amine The compound was prepared as described in Example 81 by the reaction of alcohol 26 (0.03 g, 0.107 mmole) and 3-dimethylaminopropylchloride-hydrochloride (0.17 g, 1.07 mmole), whereat an oily product was obtained (0.03 g).

$^1$H NMR (ppm, CDCl$_3$): 1.98 (p, 2H); 2.49 (s, 6H); 2.70 (t, 2H); 3.63 (t, 2H); 4.68 (s, 2H); 5.24 (s, 1H); 6.75–7.35 (m, 9H).

Example 86
N,N-dimethyl-[2-(8H-1-thia-8-aza-dibenzo[e,h]azulene-2-ylmethoxy)-ethyl]-amine The compound was prepared as described in Example 81 by the reaction of alcohol 26 (0.04 g, 0.143 mmole) and 2-dimethylaminoethylchloride-hydrochloride (0.29 g, 2.0 mmole), whereat an oily product was obtained (0.04 g).

$^1$H NMR (ppm, CDCl$_3$): 2.47 (s, 6H); 2.77 (t, 2H); 3.76 (t, 2H); 4.71 (s, 2H); 5.27 (s, 1H); 6.80–7.35 (m, 9H).

Example 87
[3-(11-fluoro-8-oxa-1-thia-dibenzo[e,h]azulene-2-ylmethoxy)-propylamine hydrochloride The compound was prepared as described in Example 81 by the reaction of alcohol 4 (0.25 g, 0.84 mmole) and 3-chloropropylamine-hydrochloride (1.53 g, 0.012 mmole), whereat an oily product was obtained, which was converted to hydrochloride (0.05 g).

$^1$H NMR (ppm, CDCl$_3$): 1.9 (m, 2H); 3.04 (m, 2H); 3.20 (m, 2H); 3.71 (m, 2H); 4.74 (s, 2H); 6.91–7.55 (m, 8H).

MS (m/z): 356.2 (MH$^+$)

Example 88
[3-(1,8-dithia-dibenzo[e,h]azulene-2-ylmethoxy]-propylamine

The compound was prepared as described in Example 81 by the reaction of alcohol 5 (0.25 g, 0.84 mmole) and 3-chloropropylamine-hydrochloride (1.54 g, 0.012 mmole), whereat an oily product was obtained (0.14 g).

$^1$H NMR (ppm, CDCl$_3$): 1.89 (m, 2H); 2.98 (t, 2H); 3.29 (bs, 2H); 3.67 (t, 2H); 4.74 (s, 2H); 7.16–7.63 (m, 9H).

MS (m/z) (ES$^+$): 354 (MH$^+$)

Example 89
N,N-dimethyl-{3-[3-(8-oxa-1-thia-dibenzo[e,h]azulene-2-yl)-propyloxy]-propyl}-amine To a solution of 3-dimethylaminopropylchloride-hydrochloride (0.65 g, 0.0041 mole) in 50% sodium hydroxide (5 ml), benzyltriethylammonium chloride (0.15 g) and a toluene solution of alcohol 15 (0.09 g, 0.29 mmole) were added. The reaction mixture was heated under vigorous stirring and reflux for 3 hours. Then it was cooled to room temperature, diluted with water and extracted with dichloromethane. After purification by column chromatography, an oily product was isolated (0.05 g).

$^1$H NMR (ppm, CDCl$_3$): 2.02 (m, 2H); 2.13 (m, 2H); 2.73 (s, 6H); 2.96 (t, 2H); 3.09 (t, 2H); 3.54 (m, 4H); 7.07 (s, 1H); 7.14–7.46 (m, 8H).

Example 90
N,N-dimethyl-{2-[3-(8-oxa-1-thia-dibenzo[e,h]azulene-2-yl)-propyloxyl-ethyl}-amine The compound was prepared as described in Example 89 by the reaction of alcohol 15 (0.09 g, 0.29 mmole) and 2-dimethylaminoethylchloride-hydrochloride (0.58 g, 0.004 mole), whereat an oily product was obtained (0.025 g).

$^1$H NMR (ppm, CDCl$_3$): 2.04 (m, 2H); 2.38 (s, 6H); 2.66 (t, 2H); 2.97 (t, 2H); 3.56 (t, 2H); 3.62 (t, 2H); 7.06 (s, 1H); 7.13–7.46 (m, 8H).

Example 91
N,N-dimethyl-{3-[3-(1,8-dithia-dibenzo[e,h]azulene-2-yl)-propyloxy]-propyl}-amine To a solution of 3-dimethylaminopropylchloride-hydrochloride (0.90 g, 0.0052 mole) in 50% sodium hydroxide (5 ml), benzyltriethylammonium chloride (0.15 g) and a toluene solution of alcohol 16 (0.12 g, 0.37 mmole) were added. The reaction mixture was heated under vigorous stirring and reflux for 3 hours. Then it was cooled to room temperature, diluted with water and extracted with dichloromethane. After purification by column chromatography, an oily product was isolated (0.035 g).

$^1$H NMR (ppm, CDCl$_3$): 1.84 (m, 2H); 2.06 (m, 2H); 2.32 (s, 6H); 2.48 (t, 2H); 3.00 (t, 2H); 3.55 (m, 4H); 7.05 (s, 1H); 7.25–7.70 (m, 8H).

Example 92
N,N-dimethyl-{2-[3-(1,8-dithia-dibenzo[e,h]azulene-2-yl)-propyloxy]-ethyl}-amine The compound was prepared as described in Example 91 by the reaction of alcohol 16 (0.21 g, 0.63 mmole) and 2-dimethylaminoethylchloride-hydrochloride (1.27 g, 0.009 mole), whereat an oily product was obtained (0.13 g).

$^1$H NMR (ppm, CDCl$_3$): 2.03 (m, 2H); 2.35 (s, 6H); 2.64 (t, 2H); 2.96 (t, 2H); 3.54 (t, 2H); 3.59 (t, 2H); 7.02 (s, 1H); 7.21–7.65 (m, 8H).

Example 93
N,N-dimethyl-{3-(8H-1-thia-dibenzo[e,h]azulene-2-ylmethoxy]-propyl}-amine To a solution of 3-dimethylaminopropylchloride-hydrochloride (1.14 g, 0.0072 mole) in 50% sodium hydroxide (5 ml), benzyltriethylammonium chloride (0.15 g) and a toluene solution of alcohol 17 (0.2 g, 0.72 mmole) were added. The reaction mixture was heated under vigorous stirring and reflux for 3 hours. Then it was cooled to room temperature, diluted with water and extracted with dichloromethane. After purification by column chromatography an oily product was isolated (0.20 g).

$^1$H NMR (ppm, CDCl$_3$): 1.93 (m, 2H); 2.37 (s, 6H); 2.57 (t, 2H); 3.67 (t, 2H); 3.75 (m, 2H); 4.75 (s, 2H); 7.20–7.55 (m, 9H).

Example 94
N,N-dimethyl-{2-(8H-1-thia-dibenzo[e,h]azulene-2-yl)-methoxyl-ethyl}-amine The compound was prepared as described in Example 93 by the reaction of alcohol 17 (0.20 g, 0.72 mmole) and 2-dimethylaminoethylchloride-hydrochloride (1.03 g, 0.007 mole), whereat an oily product was obtained (0.19 g).

$^1$H NMR (ppm, CDCl$_3$): 2.54 (s, 6H); 2.88 (t, 2H); 3.75 (m, 2H); 3.85 (t, 2H); 4.79 (s, 2H); 7.20–7.52 (m, 9H).

Example 95
N,N-dimethyl-{3-[3-(1,8-dithia-dibenzo[e,h]azulene-2-yl)-allyloxy]-propyl}-amine To a solution of 3-dimethylaminopropylchloride-hydrochloride (0.34 g, 0.0022 mole) in 50% sodium hydroxide (5 ml), benzyltriethylammonium chloride (0.15 g) and a toluene solution of alcohol 18 (0.05 g, 0.15 mmole) were added. The reaction mixture was heated under vigorous stirring and reflux for 3 hours. Then it was cooled to room temperature, diluted with water and extracted with dichloromethane. After purification by column chromatography, an oily product was isolated (0.012 g).

MS (m/z)(ES$^+$): 408.2 (MH$^+$)

Example 96
N,N-dimethyl-{2-[3-(1,8-dithia-dibenzo[e,h]azulene-2-yl)-allyloxy]-ethyl}-amine The compound was prepared as described in Example 95 by the reaction of alcohol 18 (0.11 g, 0.34 mmole) and 2-dimethylaminoethylchloride-hydrochloride (0.64 g, 0.004 mole), whereat an oily product was obtained (0.018 g).

MS (m/z) (ES$^+$): 394.2 (MH$^+$)

Example 97
N,N-dimethyl-[3-(8-benzyl-8H-1-thia-8-aza-dibenzo[e,h]azulene-2-ylmethoxy)-propyl]-amine To a solution of 3-dimethylaminopropylchloride-hydrochloride (1.2 g, 0.0054 mole) in 50% sodium hydroxide (5 ml), benzyltriethylammonium chloride (0.15 g) and a toluene solution of alcohol 19 (0.20 g, 0.54 mmole) were added. The reaction mixture was heated under vigorous stirring and reflux for 3 hours. Then it was cooled to room temperature, diluted with water and extracted with dichloromethane. After purification by column chromatography an oily product was isolated (0.15 g).

$^1$H NMNR (ppm, CDCl$_3$): 1.97 (m, 2H); 2.42 (s, 6H); 2.66 (t, 2H); 3.68 (t, 2H); 4.76 (s, 2H); 4.99 (d, 2H); 6.95–7.40 (m, 14H).

Example 98
N,N-dimethyl-[2-(8-benzyl-8H-1-thia-8-aza-dibenzo[e,h]azulene-2-ylmethoxy)-ethyl]-amine The compound was prepared as described in Example 97 by the reaction of alcohol 19 (0.20 g, 0.54 mmole) and 2-dimethylaminoethylchloride-hydrochloride (1.10 g, 0.008 mole), whereat an oily product was obtained (0.15 g).

$^1$H NMR (ppm, CDCl$_3$): 2.70 (s, 6H); 3.06 (t, 2H); 3.98 (t, 2H); 4.82 (s, 2H); 5.00 (d, 2H); 6.97–7.40 (m, 14H).

Example 99
N-methyl-[3-(11-chloro-8-oxa-1-thia-dibenzo[e,h]azulene-2-ylmethoxy)-propyl]-amine To a methanol solution of a compound of a structure I (X=O, R$_1$=R$_3$=R$_4$=R$_5$=R$_6$=R$_7$=R$_8$=R$_9$=H, R$_2$=Cl, R$_{10}$=CH$_2$OCH$_2$CH$_2$CH$_2$N(CH$_3$)$_2$) (1.79 g, 4.48 mmole, in 50 ml of methanol), sodium acetate trihydrate (3.05 g, 0.022 mole) and iodine (1.2 g, 4.7 mmole) were added. The reaction mixture was exposed to light by the use of a 500 W lamp and it was stirred at room temperature for 5 hours. When all the reactant had been reacted (the course of the reaction was followed by thin layer chromatography), sodium thiosulphate was added to the reaction mixture and the solvent was evaporated. The residue was extracted with ethyl acetate. After purification on a column, 1.2 g of an oily product were isolated.

$^1$H NMR (ppm, CDCl$_3$): 1.93 (m, 2H); 2.35–2.45 (bs, 1H); 2.5 (s, 3H); 2.80 (t, 2H); 3.66 (t, 2H); 4.73 (s, 2H); 7.18–7.47 (m, 8H).

Example 100
N-methyl-[2-(11-chloro-8-oxa-1-thia-dibenzo[e,h]azulene-2-ylmethoxy)-ethyl]-amine To a methanol solution of a compound of the structure I (X—O, R$_1$=R$_3$=R$_4$=R$_5$=R$_6$=R$_7$=R$_8$=R$_9$=H, R$_2$=Cl, R$_{10}$=CH$_2$OCH$_2$CH$_2$N(CH$_3$)$_2$) (0.47 g, 1.22 mmole, in 30 ml of methanol), sodium acetate trihydrate (0.83 g, 6.1 mmole) and iodine (0.32 g, 1.28 mmole) were added. The reaction mixture was exposed to light by the use of a 500 W lamp and it was stirred at a room temperature for 5 hours. When all the reactant had been reacted (the course of reaction was followed by thin layer chromatography), sodium thiosulphate was added to the reaction mixture and the solvent was evaporated. The dry residue was extracted with ethyl acetate. After purification on a column, 0.29 g of an oily product were isolated.

$^1$H NMR (ppm, CDCl$_3$): 2.26 (bs, 1H); 2.5 (s, 3H); 2.85 (t, 2H); 3.71 (t, 2H); 4.75 (s, 2H); 7.18–7.47 (m, 8H).

Example 101
N-methyl-[3-(8-oxa-1-thia-dibenzo[e,h]azulene-2-ylmethoxy)-propyl]-amine To a methanol solution of a compound of a structure I (X=O, R$_1$=R$_2$=R$_3$=R$_4$=R$_5$=R$_6$=R$_7$=R$_8$=R$_9$=H, R$_{10}$=CH$_2$OCH$_2$CH$_2$CH$_2$N(CH$_3$)$_2$) (1.18 g, 0.49 mmole, in 10 ml of methanol) sodium acetate trihydrate (0.33 g, 2.46 mmole) and iodine (0.13 g, 0.52 mmole) were added. The reaction mixture was exposed to the light by the use of 500 W lamp and it was stirred at a room temperature for 5 hours. Subsequently after all reactant was reacted (the course of reaction was followed by thin layer chromatography) to the reaction mixture sodium thiosulphate was added and the solvent was evaporated. The residue was extracted with ethyl acetate. After purification on a column 0.1 g of oily product were isolated.

$^1$H NMR (ppm, CDCl$_3$): 2.2 (m, 2H); 2.72 (s, 3H); 3.15 (m, 2H); 3.72 (t, 2H); 4.75 (s, 2H); 7.15–7.47 (m, 9H); 9.44 (bs, 1H).

Example 102
N-methyl-[3-(1,8-dithia-dibenzo[e,h]azulene-2-ylmethoxy)-propyl]-amine To a methanol solution of a compound of a structure I (X—S, $R_1=R_2=R_3=R_4=R_5=R_6=R_7=R_8=R_9=H$, $R_{10}=CH_2OCH_2CH_2CH_2N(CH_3)_2$) (0.14 g, 0.37 mmole in 10 ml of methanol), sodium acetate trihydrate (0.25 g, 1.83 mmole) and iodine (0.1 g, 0.39 mmole) were added. The reaction mixture was exposed to light by the use of a 500 W lamp and it was stirred at room temperature for 5 hours. When all reactant has been reacted (the course of reaction was followed by thin layer chromatography), sodium thiosulphate was added to the reaction mixture and the solvent was evaporated. The residue was extracted with ethyl acetate. After purification on a column, 0.09 g of an oily product were isolated.

$^1$H NMR (ppm, CDCl$_3$): 2.17 (m, 2H); 2.69 (s, 3H); 3.15 (t, 2H); 3.76 (t, 2H); 4.5–4.7 (bs, 1H); 4.79 (s, 2H); 7.20–7.63 (m, 9H).

Example 103
2-bromomethyl-1,8-dithia-dibenzo[e,h]azulene

The solution of alcohol 5 (0.5 g, 1.69 mmole) in a 47% hydrobromic acid (1.4 ml) was heated under reflux for 3 hours. When all reactant has been reacted (the course of reaction was followed by thin layer chromatography), water (10 ml) was added to the reaction mixture and the product was extracted with ethyl acetate. The raw product was purified by chromatography on a column. There were isolated 0.5 g of an oily product.

$^1$H NMR (ppm, CDCl$_3$): 4.80 (s, 2H); 7.27–7.65 (m, 9H).

Example 104
(1,8-dithia-dibenzo[e,h]azulene-2-yl)-acetonitrile

To an ethanol solution of 2-bromomethyl-1,8-dithia-dibenzo[e,h]azulene (0.5 g, 1,4 mmole in 8 ml of ethanol), sodium cyanide (0.105 g, 2.1 mmole) was added and the reaction mixture was heated under reflux for 8 hours. When all reactant had been reacted (the course of reaction was followed by thin layer chromatography), the solvent was evaporated and the dry residue was extracted in a system diethyl ether/water. 0.4 g of an oily product were isolated.

IR (film): 3055 cm$^{-1}$, 2972 cm$^{-1}$, 2922 cm$^{-1}$, 2851 cm$^{-1}$, 2252 cm$^{-1}$ (CN), 1713 cm$^{-1}$, 1476 cm$^{-1}$

Example 105
2-(1,8-dithia-dibenzo[e,h]azulene-2yl)-ethylamine

To a suspension of LiAlH$_4$ in the dry ether (0.1 g, 2.62 mmole in 20 ml of ether), an ether solution of a compound of the structure I (X=S, $R_1=R_2=R_3=R_4=R_5=R_6=R_7=R_8=R_9=H$, $R_{10}=CH_2CN$) (0.4 g, 1.31 mmole) was added dropwise. The reaction mixture was stirred at room temperature for 4 hours. When all amount of ester had been reacted (the course of reaction was followed by thin layer chromatography), the excess of LiAlH$_4$ was decomposed by the addition of diethlyether and water. The obtained white precipitate was filtered off and, after drying over anhydrous Na$_2$SO$_4$, the filtrate was evaporated under the reduced pressure. The raw product was purified by chromatography on a column. 0.025 g of an oily product were isolated.

MS m/z (ES$^+$): 293.2 (M-NH$_2$); 310.2 (MH$^+$).

Preparation of Aldehydes

To a chloromethane solution of alcohol (0.002 mole/15 ml) (Table 1) dipyridine chrome (VI) oxide (pyridyl-dichromate, PDC, 0.003 mole) was added. The reaction mixture was stirred at room temperature within a period of 3 to 18 hours. To the reaction mixture diethyl ether (20 ml) was added and the diluted reaction mixture was purified on a florisil column. The obtained product was additionally purified on a silica gel column.

According to the process of preparation of aldehydes, starting from an appropriate alcohol (Table 1, compounds 1, 3, 4 and 5) there were obtained dibenzoazulene derivatives, wherein $R_1$, $R_3$, $R_4$, $R_5$, $R_6$, $R_7$, $R_8$ and $R_9$—H, $R_{10}$=CHO and $R_2$, $R_3$, $R_4$ and X have the meanings shown in Table 2.

TABLE 2

| Comp. | X | $R_2$ | $R_3$ | $R_4$ | $^1$H NMR (ppm, CDCl$_3$) |
|---|---|---|---|---|---|
| 28 | O | F | H | H | 7.07–7.52(m, 7H); 7.98(s, 1H); 9.98(s, 2H) |
| 29 | O | Cl | H | H | 7.16–7.60(m, 7H); 8.01(s, 1H); 9.99(s, 2H) |
| 30 | O | H | H | H | 7.2–7.68(m, 7H); 7.95(s, 1H); 9.99(s, 2H) |
| 31 | S | H | H | H | 7.33–7.68(m, 7H); 7.95(s, 1H); 9.99(s, 2H) |

The following compounds described in Examples 106–113 were prepared from aldehydes disclosed in Table 2 and the corresponding phosphorous-ylides according to the process described in Example 106.

Example 106
4-(11-fluoro-8-oxa-1-thia-dibenzo[e,h]azulene-2-yl)-acrylic acid methyl ester To a solution of aldehyde 28 (0.07 g, 0.0024 mole) in toluene (10 ml), ylide III (methyl(triphenyl)phosphoranylide acetate) (0.08 g, 0.0024 mole) was added. The reaction mixture was stirred under reflux for 4 hours and then it was cooled to room temperature, evaporated to dryness and extracted with ethyl acetate. After purification by column chromatography a crystalline product (0.03 g) was isolated.

$^1$H NMR (ppm, CDCl$_3$): 3.82 (s, 3H); 6.31 (d, 1H, J=15.67 Hz); 7.01–7.07 (m, 2H); 7.12–7.17 (m, 1H); 7.21–7.46 (m, 4H); 7.48 (s, 1H); 7.80 (d, 1H, J=15.69 Hz).

Example 107
4-(11-chloro-8-oxa-1-thia-dibenzo[e,h]azulene-2-yl)-acrylic acid methyl ester To a solution of aldehyde 29 (0.15 g, 0.48 mmole) in tetrahydrofuran (20 ml), ylide III (0.24 g, 0.72 mmole) was added. The reaction mixture was stirred under reflux for 4 hours and then it was cooled to room temperature, evaporated to dryness and extracted with ethyl acetate. After purification by column chromatography, a crystalline product (0.08 g) was isolated.

$^1$H NMR (ppm, CDCl$_3$): 3.82 (s, 3H); 6.30 (d, 1H, J=15.68 Hz); 7.08–7.57 (m, 8H); 7.80 (d, 1H, J=15.68 Hz).

Example 108
4-(11-fluoro-8-oxa-1-thia-dibenzo[e,h]azulene-2-yl)-but-3-ene-2-one To a solution of aldehyde 15 (0.14 g, 0.47 mmole) in toluene (10 ml), ylide IV (acetylmethylentriphenylphosphoran) (0.15 g, 0.47 mmole) was added. The reaction mixture was stirred under reflux for 4 hours and then it was cooled to room temperature, evaporated to dryness and extracted with ethyl acetate. After purification by column chromatography a crystalline product (0.08 g) was isolated.

Example 109
4-(11-chloro-8-oxa-1-thia-dibenzo[e,h]azulene-2-yl)-but-3-ene-2-one To a solution of aldehyde 29 (0.15 g, 0.48 mmole) in tetrahydrofuran (10 ml), ylide IV (0.15 g, 0.47 mmole) was added. The reaction mixture was stirred under reflux for 4 hours and then it was cooled to room temperature, evaporated to dryness and extracted with ethyl acetate. After purification by column chromatography, a crystalline product (0.08 g) was isolated.

$^1$H NMR (ppm, CDCl$_3$): 2.35 (s, 3H); 6.60 (d, 1H, J=15.85 Hz); 7.02–7.08 (m, 2H); 7.14–7.17 (m, 1H); 7.22–7.48 (m, 4H); 7.52 (s, 1H); 7.65 (d, 1H, J=15.86 Hz).

Example 109
4-(11-chloro-8-oxa-1-thia-dibenzo[e,h]azulene-2-yl)-but-3-ene-2-one To a solution of aldehyde 29 (0.15 g, 0.48 mmole) in tetrahydrofuran (10 ml), ylide IV (0.15 g, 0.47 mmole) was added. The reaction mixture was stirred under reflux for 4 hours and then it was cooled to room temperature, evaporated to dryness and extracted with ethyl acetate. After purification by column chromatography, a crystalline product (0.08 g) was isolated.

$^1$H NMR (ppm, CDCl$_3$): 2.39 (s, 3H); 6.61 (d, 1H, J=15.87 Hz); 7.01–7.60 (m, 8H); 7.65 (d, 1H, J=15.86 Hz).

Example 110
3-(11-fluoro-8-oxa-1-thia-dibenzo[e,h]azulene-2-yl)-acrylic acid The hydrolysis of the ester prepared as described in Example 106 (0.03 g, 0.085 mmole) was performed with 2 M KOH (reflux, 2 to 5 hours) and by acidifying the reaction mixture with concentrated HCl. The obtained crystalline product was filtered off and washed with water (0.02 g).

$^1$H NMR (ppm, CDCl$_3$): 6.3 (d, 1H); 7.02–7.09 (m, 2H); 7.12–7.17 (m, 1H); 7.22–7.48 (m, 4H); 7.53 (s, 1H); 7.9 (d, 1H).

Example 111
3-(11-fluoro-8-oxa-1-thia-dibenzo[e,h]azulene-2-yl)-propionic acid To an ethanol solution (10 ml) of the acid prepared in Example, 107, 5% Pd/C (5 mg) moistened with water (50%) was added. The reaction mixture was stirred at room temperature in hydrogen atmosphere at the pressure of 300 kPa. After the filtration of the catalyst and the evaporation of the solvent, a product was obtained, which was purified by column chromatography on a silica gel column.

$^1$H NMR (CDCl$_3$): 2.83 (t, 2H); 3.23 (t, 2H); 6.93–7.45 (m, 7H).

Example 112
Methyl-3-(8-oxa-1-thia-dibenzo[e,h]azulene-2-yl)-propenoate

To a solution of aldehyde 30 (0.6 g, 2.16 mmole) in toluene (20 ml), methyl (triphenylphosphoraniliden)acetate (0.72 g, 2.16 mmole) was added. The reaction mixture was stirred under reflux for 4 hours and then it was cooled to room temperature, evaporated to dryness and extracted with ethyl acetate. After purification by column chromatography, a crystalline product (0.90 g) was isolated.

$^1$H NMR (ppm, CDCl$_3$): 3.82 (s, 3H); 6.30 (d, 1H, J=15.68 Hz); 7.20–7.74 (m, 9H); 7.84 (d, 1H, J=15.68 Hz).

Example 113
Methyl-3-(1,8-dithia-dibenzo[e,h]azulene-2-yl)-propenoate

To a solution of aldehyde 31 (0.25 g, 0.89 mmole) in toluene (20 ml), methyl (triphenylphosphoraniliden)acetate (0.28 g, 0.85 mmole) was added. The reaction mixture was stirred under reflux for 4 hours and then it was cooled to room temperature, evaporated to dryness and extracted with ethyl acetate. After purification by column chromatography, a crystalline product (0.25 g) was isolated.

$^1$H NMR (ppm, CDCl$_3$): 3.82 (s, 3H); 6.30 (d, 1H, J=15.68 Hz); 7.20–7.74 (m, 9H); 7.84 (d, 1H, J=15.68 Hz).

What is claimed is:

1. A compound of formula I or pharmacologically acceptable salts thereof and hydrates thereof

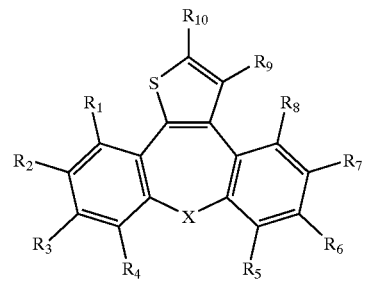

I wherein

X represents CH$_2$, or a heteroatom selected from the group consisting of O, S, S(=O), S(=O)$_2$ or NR$_{13}$ wherein R$_{13}$ is hydrogen, C$_{1-6}$ alkyl, C$_{1-6}$ alkylcarbonyl, arylcarbonyl, C$_{1-6}$ alkylsulfonyl, or arylsulfonyl;

each R$_1$, R$_2$, R$_3$, R$_4$, R$_5$, R$_6$, R$_7$, R$_8$ and R$_9$, independently represents hydrogen, fluoro, chloro, bromo; or C$_1$–C$_7$ alkyl, C$_2$–C$_7$ alkenyl; monocyclic or bicyclic aryl group having from 6 to 10 carbon atoms and alternating double bonds between carbon atoms and said aryl group can be unsubstituted or substituted with fluoro, chloro, bromo, hydroxy, C$_1$–C$_7$ alkyl, C$_1$–C$_7$ alkoxy, aryloxy, wherein aryl has the meaning as defined above, C$_1$–C$_7$ alkylthio, arylthio wherein aryl has the meaning as defined above, C$_1$–C$_7$ alkylsulfonyl, cyano, or amino; C$_1$–C$_7$ mono or di-C$_1$–C$_7$ substituted amino, heteroaryl which is a monocyclic or bicyclic aromatic hydrocarbon containing at least one heteroatom selected from O, S or N optionally said heteroaryl can be unsubstituted or substituted with fluoro, chloro, bromo, CF$_3$, methyl, ethyl or propyl; or halomethyl, hydroxy, C$_1$–C$_7$ alkoxy, aryloxy wherein aryl has the meaning as defined above, C$_1$–C$_7$ alkylthio, arylthio wherein aryl has the meaning as defined above, C$_1$–C$_7$ alkylsulfonyl, cyano, amino, C$_1$–C$_7$ mono- or di-C$_1$–C$_7$ substituted amino, C$_1$–C$_7$ hydroxycarbonyl, C$_1$–C$_7$ alkanoyloxycarbonyl, carbamoyl, mono-N-(C$_1$–C$_7$) alkylcarbamoyl, di-N,N-(C$_1$–C$_7$)alkylcarbamoyl, C$_1$–C$_7$ alkyloxycarbonyl, aryloxycarbonyl, C$_1$–C$_7$ alkylcarbonyl, arylcarbonyl;

R$_{10}$ represents C$_2$–C$_{15}$ alkyl, C$_2$–C$_{15}$ alkenyl, C$_2$–C$_{15}$ alkynyl, aryl or heteroaryl wherein aryl and heteroaryl have the meaning as defined above, C$_1$–C$_{15}$ haloalkyl, C$_1$–C$_{15}$ hydroxyalkyl, C$_1$–C$_{15}$ alkyloxy, C$_1$–C$_{15}$ alkylthio, C$_3$–C$_{15}$ alkylcarbonyl, C$_2$–C$_{15}$ hydroxycarbonyl, C$_3$–C$_{15}$ alkyloxycarbonyl, C$_1$–C$_{15}$ alkylsulfonyl, arylsulfonyl or C$_1$–C$_{15}$ alkylarylsulfonyl wherein aryl has the meaning as defined above, CH=CHCH$_2$OH, CH=CHCH$_2$O(CH$_2$)$_n$-A, or C$_1$–C$_{15}$ alkylamino represented by the formula (CH$_2$)n-A wherein n is an integer from 1 to 15, optionally one or more methylene groups can be substituted with an oxygen or sulphur atom A represents saturated or unsaturated a five- or six-membered ring having from one to three heteroatoms selected from the group consisting of O, S, N or combinations thereof, or a group of the formula

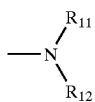

wherein
R[11] and R[12] independently represent hydrogen, $C_1$–$C_7$ alkyl, $C_2$–$C_7$ alkenyl, $C_2$–$C_7$ alkynyl, aryl or heteroaryl wherein aryl and heteroaryl have the meaning as defined above, or a saturated or unsaturated five- or six-membered ring having from one to three heteroatoms selected from the group consisting of O, S, N or combinations thereof.

2. The compound or salt thereof or hydrate thereof according to claim 1, wherein $R_{10}$ represents $CH_2OH$, $CH{=}CHCH_2OH$ or $CH_2CH_2CH_2OH$.

3. The compound or salt thereof or hydrate thereof according to claim 1, wherein $R_{10}$ represents $(CH_2)_nA$, $CH_2O(CH_2)_n\text{-}A$, $CH{=}CHCH_2O(CH_2)_n\text{-}A$ or $CH_2CH_2CH_2O(CH_2)_n\text{-}A$ wherein A and n are as defined in claim 1.

4. The compound or salt thereof or hydrate thereof according to claim 3, wherein A represents morpholine-4-yl, piperidine-1-yl or pyrrolidine-1-yl.

5. The compound and or salt thereof or hydrate thereof according to claim 3, wherein A represents

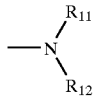

wherein $R_{11}$ and $R_{12}$ are as defined in claim 1.

6. The compound or salt thereof or hydrate thereof according to claim 5, wherein $R_{11}$ and $R_{12}$ represent H, —$CH_3$ or —$CH_2CH_3$.

7. The compound or salt thereof or hydrate thereof according to claim 1, wherein $R_2$ represents H, $SCH_3$, F, Cl, Br or $CH_3$.

8. The compound or salt thereof or hydrate thereof according to claim 1, wherein $R_3$ represents H, $OCH_3$, F, Cl, Br, $CF_3$ or $CH_3$.

9. The compound or salt thereof or hydrate thereof according to claim 1, wherein $R_4$ represents H, F, Cl or $CH_3$.

10. The compound or salt thereof or hydrate thereof according to claim 1, wherein $R_6$ represents H, F or Cl.

11. The compound of formula I according to claim 1 selected from the group consisting of:
dimethyl-[3-(8-oxa-1-thia-dibenzo[e,h]azulene-2-ylmethoxy)-propyl]-amine hydrochloride,
dimethyl-[2-(8-oxa-1-thia-dibenzo[e,h]azulene-2-ylmethoxy)-ethyl]-amine hydrochloride,
4-[2-(8-oxa-1-thia-dibenzo[e,h]azulene-2-ylmethoxy)-ethyl]-morpholine hydrochloride,
1-[2-(8-oxa-1-thia-dibenzo[e,h]azulene-2-ylmethoxy)-ethyl]-piperidine hydrochloride,
1-[2-(8-oxa-1-thia-dibenzo[e,h]azulene-2-ylmethoxy)-ethyl]-pyrrolidine hydrochloride,
[3-(9-chloro-8-oxa-1-thia-dibenzo[e,h]azulene-2-ylmethoxy)-propyl]-dimethyl-amine,
[2-(9-chloro-8-oxa-1-thia-dibenzo[e,h]azulene-2-ylmethoxy)-ethyl]-dimethyl-amine,
4-[2-(9-chloro-8-oxa-1-thia-dibenzo[e,h]azulene-2-ylmethoxy)-ethyl]-morpholine,
1-[2-(9-chloro-8-oxa-1-thia-dibenzo[e,h]azulene-2-ylmethoxy)-ethyl]-piperidine,
1-[2-(9-chloro-8-oxa-1-thia-dibenzo[e,h]azulene-2-ylmethoxy)-ethyl]-pyrrolidine,
[3-(11-chloro-8-oxa-1-thia-dibenzo[e,h]azulene-2-ylmethoxy)-propyl]-dimethyl-amine,
[2-(11-chloro-8-oxa-1-thia-dibenzo[e,h]azulene-2-ylmethoxy)-ethyl]-dimethyl-amine,
4-[2-(11-chloro-8-oxa-1-thia-dibenzo[e,h]azulene-2-ylmethoxy)-ethyl]-morpholine,
1-[2-(11-chloro-8-oxa-1-thia-dibenzo[e,h]azulene-2-ylmethoxy)-ethyl]-piperidine,
1-[2-(11-chloro-8-oxa-1-thia-dibenzo[e,h]azulene-2-ylmethoxy)-ethyl]-pyrrolidine,
[3-(11-fluoro-8-oxa-1-thia-dibenzo[e,h]azulene-2-ylmethoxy)-propyl]-dimethyl-amine hydrochloride,
[2-(11-fluoro-8-oxa-1-thia-dibenzo[e,h]azulene-2-ylmethoxy)-ethyl]-dimethyl-amine hydrochloride,
4-[2-(11-fluoro-8-oxa-1-thia-dibenzo[e,h]azulene-2-ylmethoxy)-ethyl]-morpholine hydrochloride,
1-[2-(11-fluoro-8-oxa-1-thia-dibenzo[e,h]azulene-2-ylmethoxy)-ethyl]-piperidine hydrochloride,
1-[2-(11-fluoro-8-oxa-1-thia-dibenzo[e,h]azulene-2-ylmethoxy)-ethyl]-pyrrolidine hydrochloride,
[3-(1,8-dithia-dibenzo[e,h]azulene-2-ylmethoxy)-propyl]-dimethyl-amine hydrochloride,
[2-(1,8-dithia-dibenzo[e,h]azulene-2-ylmethoxy)-ethyl]-dimethyl-amine hydrochloride,
4-[2-(1,8-dithia-dibenzo[e,h]azulene-2-ylmethoxy)-ethyl]-morpholine hydrochloride,
1-[2-(1,8-dithia-dibenzo[e,h]azulene-2-ylmethoxy)-ethyl]-piperidine hydrochloride,
1-[2-(1,8-dithia-dibenzo[e,h]azulene-2-ylmethoxy)-ethyl]-pyrrolidine hydrochloride,
[3-(11-fluoro-1,8-dithia-dibenzo[e,h]azulene-2-ylmethoxy)-propyl]-dimethyl-amine hydrochloride,
[2-(11-fluoro-1,8-dithia-dibenzo[e,h]azulene-2-ylmethoxy)-ethyl]-dimethyl-amine hydrochloride,
4-[2-(11-fluoro-1,8-dithia-dibenzo[e,h]azulene-2-ylmethoxy)-ethyl]-morpholine hydrochloride,
1-[2-(11-fluoro-1,8-dithia-dibenzo[e,h]azulene-2-ylmethoxy)-ethyl]-piperidine hydrochloride,
1-[2-(11-fluoro-1,8-dithia-dibenzo[e,h]azulene-2-ylmethoxy)-ethyl]-pyrrolidine hydrochloride,
[3-(11-chloro-1,8-dithia-dibenzo[e,h]azulene-2-ylmethoxy)-propyl]-dimethyl-amine hydrochloride,
[2-(11-chloro-1,8-dithia-dibenzo[e,h]azulene-2-ylmethoxy)-ethyl]-dimethyl-amine hydrochloride,
4-[2-(11-chloro-1,8-dithia-dibenzo[e,h]azulene-2-ylmethoxy)-ethyl]-morpholine hydrochloride,
1-[2-(11-chloro-1,8-dithia-dibenzo[e,h]azulene-2-ylmethoxy)-ethyl]-piperidine hydrochloride,
1-[2-(11-chloro-1,8-dithia-dibenzo[e,h]azulene-2-ylmethoxy)-ethyl]-pyrrolidine hydrochloride,
[3-(11-bromo-1,8-dithia-dibenzo[e,h]azulene-2-ylmethoxy)-propyl]-dimethyl-amine hydrochloride,
[2-(11-bromo-1,8-dithia-dibenzo[e,h]azulene-2-ylmethoxy)-ethyl]-dimethyl-amine hydrochloride,
4-[2-(11-bromo-1,8-dithia-dibenzo[e,h]azulene-2-ylmethoxy)-ethyl]-morpholine,
1-[2-(11-bromo-1,8-dithia-dibenzo[e,h]azulene-2-ylmethoxy)-ethyl]-piperidine, 1-[2-(11-bromo-1,8-dithia-dibenzo[e,h]azulene-2-ylmethoxy)-ethyl]-pyrrolidine,
[3-(10-trifluoromethyl-1,8-dithia-dibenzo[e,h]azulene-2-ylmethoxy)-propyl]-dimethyl-amine,
dimethyl-[2-(10-trifluoromethyl-1,8-dithia-dibenzo[e,h]azulene-2-ylmethoxy)-ethyl]-amine hydrochloride,
4-[2-(10-trifluoromethyl-1,8-dithia-dibenzo[e,h]azulene-2-ylmethoxy)-ethyl]-morpholine,
1-[2-(10-trifluoromethyl-1,8-dithia-dibenzo[e,h]azulene-2-ylmethoxy)-ethyl]-piperidine hydrochloride,
1-[2-(10-trifluoromethyl-1,8-dithia-dibenzo[e,h]azulene-2-ylmethoxy)-ethyl]-pyrrolidine hydrochloride,
[3-(10-chloro-1,8-dithia-dibenzo[e,h]azulene-2-ylmethoxy)-propyl]-dimethyl-amine,
[2-(10-chloro-1,8-dithia-dibenzo[e,h]azulene-2-ylmethoxy)-ethyl]-dimethyl-amine hydrochloride,
1-[2-(10-chloro-1,8-dithia-dibenzo[e,h]azulene-2-ylmethoxy)-ethyl]-piperidine hydrochloride,
1-[2-(10-chloro-1,8-dithia-dibenzo[e,h]azulene-2-ylmethoxy)-ethyl]-pyrrolidine,
[3-(10-bromo-1,8-dithia-dibenzo[e,h]azulene-2-ylmethoxy)-propyl]-dimethyl-amine hydrochloride,
[2-(10-bromo-1,8-dithia-dibenzo[e,h]azulene-2-ylmethoxy)-ethyl]-dimethyl-amine hydrochloride,
1-[2-(10-bromo-1,8-dithia-dibenzo[e,h]azulene-2-ylmethoxy)-ethyl]-piperidine hydrochloride,
1-[2-(10-bromo-1,8-dithia-dibenzo[e,h]azulene-2-ylmethoxy)-ethyl]-pyrrolidine,
[2-(10-bromo-1,8-dithia-dibenzo[e,h]azulene-2-ylmethoxy)-propyl]-dimethyl-amine hydrochloride,
[3-(9,11-dimethyl-1,8-dithia-dibenzo[e,h]azulene-2-ylmethoxy)-propyl]-dimethyl-amine hydrochloride,
[2-(9,11-dimethyl-1,8-dithia-dibenzo[e,h]azulene-2-ylmethoxy)-ethyl]-dimethyl-amine hydrochloride,
1-[2-(9,11-dimethyl-1,8-dithia-dibenzo[e,h]azulene-2-ylmethoxy)-ethyl]-pyrrolidine hydrochloride,
[3-(10,11-dichloro-1,8-dithia-dibenzo[e,h]azulene-2-ylmethoxy)-propyl]-dimethyl-amine hydrochloride,
[2-(10,11-dichloro-1,8-dithia-dibenzo[e,h]azulene-2-ylmethoxy)-ethyl]-dimethyl-amine hydrochloride,
4-[2-(10,11-dichloro-1,8-dithia-dibenzo[e,h]azulene-2-ylmethoxy)-ethyl]-morpholine hydrochloride,
1-[2-(10,11-dichloro-1,8-dithia-dibenzo[e,h]azulene-2-ylmethoxy)-ethyl]-piperidine hydrochloride,
1-[2-(10,11-dichloro-1,8-dithia-dibenzo[e,h]azulene-2-ylmethoxy)-ethyl]-pyrrolidine hydrochloride,
[3-(9-chloro-11-fluoro-1,8-dithia-dibenzo[e,h]azulene-2-ylmethoxy)-propyl]-dimethyl-amine hydrochloride,
[2-(9-chloro-11-fluoro-1,8-dithia-dibenzo[e,h]azulene-2-ylmethoxy)-ethyl]-dimethyl-amine hydrochloride,
4-(11-fluoro-8-oxa-1-thia-dibenzo[e,h]azulene-2-yl)-but-3-ene-2-one,
4-(11-chloro-8-oxa-1-thia-dibenzo[e,h]azulene-2-yl)-but-3-ene-2-one,
3-(11-fluoro-8-oxa-1-thia-dibenzo[e,h]azulene-2-yl)-acrylic acid,
3-(11-fluoro-8-oxa-1-thia-dibenzo[e,h]azulene-2-yl)-propionic acid,
3-(11-chloro-8-oxa-1-thia-dibenzo[e,h]azulene-2-ylmethoxy)-propylamine,
3-(8-oxa-1-thia-dibenzo[e,h]azulene-2-ylmethoxy)-propylamine,
N,N-dimethyl-[3-(11-methylsulfanyl-1,8-dithia-dibenzo[e,h]azulene-2-ylmethoxy)-propyl]-amine,
N,N-dimethyl-[2-(11-methylsulfanyl-1,8-dithia-dibenzo[e,h]azulene-2-ylmethoxy)-ethyl]-amine,
N,N-dimethyl-[3-(10-methyl-1,8-dithia-dibenzo[e,h]azulene-2-ylmethoxy)-propyl]-amine,
N,N-dimethyl-[2-(10-methyl-1,8-dithia-dibenzo[e,h]azulene-2-ylmethoxy)-ethyl]-amine,
N,N-dimethyl-[3-(11-methyl-1,8-dithia-dibenzo[e,h]azulene-2-ylmethoxy)-propyl]-amine,
N,N-dimethyl-[2-(11-methyl-1,8-dithia-dibenzo[e,h]azulene-2-ylmethoxy)-ethyl]-amine,
N,N-dimethyl-[3-(10-methoxy-8-oxa-1-thia-dibenzo[e,h]azulene-2-ylmethoxy)-propyl]-amine,
N,N-dimethyl-[2-(10-methoxy-8-oxa-1-thia-dibenzo[e,h]azulene-2-ylmethoxy)-ethyl]-amine,
1-(2-(10-methoxy-8-oxa-1-thia-dibenzo[e,h]azulene-2-ylmethoxy)-ethyl]-piperidine,
1-(2-(10-methoxy-8-oxa-1-thia-dibenzo[e,h]azulene-2-ylmethoxy)-ethyl]-pyrrolidine,
3-(10-methoxy-8-oxa-1-thia-dibenzo[e,h]azulene-2-ylmethoxy)-propylamine,
N,N-dimethyl-[3-(6-chloro-1,8-dithia-dibenzo[e,h]azulene-2-ylmethoxy)-propyl]-amine,
N,N-dimethyl-[2-(6-chloro-1,8-dithia-dibenzo[e,h]azulene-2-ylmethoxy)-ethyl]-amine,
3-(6-chloro-1,8-dithia-dibenzo[e,h]azulene-2-ylmethoxy)-propyl]-amine,
N,N-dimethyl-[3-(10-fluoro-1,8-dithia-dibenzo[e,h]azulene-2-ylmethoxy)-propyl]-amine,
N,N-dimethyl-[2-(10-fluoro-1,8-dithia-dibenzo[e,h]azulene-2-ylmethoxy)-ethyl]-amine,
[2-(3-dimethylamino-propoxymethyl)-1-thia-8-aza-dibenzo[e,h]azulene-8-yl)-phenyl-methanon,
[2-(2-dimethylamino-ethoxymethyl)-1-thia-8-aza-dibenzo[e,h]azulene-8-yl)-phenyl-methanon,
N,N-dimethyl-[3-(8H-1-thia-8-aza-dibenzo[e,h]azulene-2-ylmethoxy)-propyl]-amine,
N,N-dimethyl-[2-(8H-1-thia-8-aza-dibenzo[e,h]azulene-2-ylmethoxy)-ethyl]-amine,
[3-(11-fluoro-8-oxa-1-thia-dibenzo[e,h]azulene-2-ylmethoxy)-propylamine hydrochloride,
[3-(1,8-dithia-dibenzo[e,h]azulene-2-ylmethoxy]-propylamine,
N,N-dimethyl-{3-[3-(8-oxa-1-thia-dibenzo[e,h]azulene-2-yl)-propyloxy]-propyl}-amine,
N,N-dimethyl-{2-[3-(8-oxa-1-thia-dibenzo[e,h]azulene-2-yl)-propyloxy]-ethyl}-amine,
N,N-dimethyl-{3-[3-(1,8-dithia-dibenzo[e,h]azulene-2-yl)-propyloxy]-propyl}-amine,
N,N-dimethyl-{2-[3-(1,8-dithia-dibenzo[e,h]azulene-2-yl)-propyloxy]-ethyl}-amine,
N,N-dimethyl-{3-(8H-1-thia-dibenzo[e,h]azulene-2-yl)-methoxy]-propyl}-amine,
N,N-dimethyl-{2-(8H-1-thia-dibenzo[e,h]azulene-2-yl)-methoxy]-ethyl}-amine,
N,N-dimethyl-{3-[3-(1,8-dithia-dibenzo[e,h]azulene-2-yl)-allyloxy]-propyl}-amine,
N,N-dimethyl-{2-[3-(1,8-dithia-dibenzo[e,h]azulene-2-yl)-allyloxy]-ethyl}-amine,
N-methyl-[3-(11-chloro-8-oxa-1-thia-dibenzo[e,h]azulene-2-ylmethoxy)-propyl]-amine, N-methyl-[2-(11-chloro-8-oxa-1-thia-dibenzo[e,h]azulene-2-ylmethoxy)-ethyl]-amine,
N-methyl-[3-(8-oxa-1-thia-dibenzo[e,h]azulene-2-ylmethoxy)-propyl]-amine,
N-methyl-[3-(1,8-dithia-dibenzo[e,h]azulene-2-ylmethoxy)-propyl]-amine, 2-bromomethyl-1,8-dithia-dibenzo[e,h]azulene, and
2-(1,8-dithia-dibenzo[e,h]azulene-2-yl)-ethylamine, and salts and hydrates thereof.

12. The compound of claim 1 or salt thereof or hydrate wherein $R_{10}$ represents, $C_1$–$C_{15}$ hydroxyalkyl, or $C_1$–$C_{15}$ alkylamino represented by the formula $(CH_2)_n$-A.

13. The compound of claim 12 wherein said heteroaryl group is selected from the group consisting of thiophene, pyrrole, imidazole, pyridine, oxazole, thiazole, pyrazole, tetrazole, pyrimidine, pyrazine, and triazine.

14. The compound of claim 1 wherein said heteroaryl group is selected from the group consisting of thiophene, pyrrole, imidazole, pyridine, oxazole, thiazole, pyrazole, tetrazole, pyrimidine, pyrazine and triazine.

15. The compound of claim 1 wherein the compound of Formula I is [2-(11-chloro-8-oxa-1-thia-dibenzo[e,h]azulene-2-ylmethoxy)-ethyl]-dimethyl-amine.

16. A method for the treatment of rheumatoid arthritis comprising administering to a subject a therapeutically effective amount of a compound or a pharmacologically acceptable salt or hydrate thereof according to claim 1.

17. The method according to claim 16, wherein $R_{10}$ represents $CH_2OH$, $CH{=}CHCH_2OH$ or $CH_2CH_2CH_2OH$.

18. The method according to claim 16, wherein $R_{10}$ represents $(CH_2)_nA$, $CH_2O(CH_2)_n$-A, $CH{=}CHCH_2O(CH_2)_n$-A or $CH_2CH_2CH_2O(CH_2)_n$-A.

19. The method according to claim 16, wherein A represents morpholine-4-yl, piperidine-1-yl or pyrrolidine-1-yl.

20. The method according to claim 16, wherein A represents

wherein $R_{11}$ and $R_{12}$ are as defined in claim 1.

21. The method of claim 16 wherein $R_{11}$ and $R_{12}$ represent H, —$CH_3$ or —$CH_2CH_3$.

22. The method of claim 16 wherein $R_2$ represents H, $SCH_3$, F, Cl, Br or $CH_3$.

23. The method of claim 16 wherein $R_3$ represents H, $OCH_3$, F, Cl, Br, $CF_3$ or $CH_3$.

24. The method of claim 16 wherein $R_4$ represents H, F, Cl or $CH_3$.

25. The method of claim 16 wherein $R_6$ represents H, F or Cl.

26. The method according to claim 16 wherein $R_{10}$ represents $C_1$–$C_{15}$ hydroxyalkyl or $C_1$–$C_{15}$ alkylamino represented by the formula $(CH_2)_n$-A.

27. The method of claim 26 wherein said heteroaryl group is selected from the group consisting of thiophene, pyrrole, imidazole, pyridine, oxazole, thiazole, pyrazole, tetrazole, pyrimidine, pyrazine and triazine.

28. The method of claim 16 wherein said heteroaryl group is selected from the group consisting of thiophene, pyrrole, imidazole, pyridine, oxazole, thiazole, pyrazole, tetrazole, pyrimidine, pyrazine and triazine.

29. The method of claim 16 wherein the compound of formula I is selected from the group consisting of:
dimethyl-[3-(8-oxa-1-thia-dibenzo[e,h]azulene-2-ylmethoxy)-propyl]-amine hydrochloride,
dimethyl-[2-(8-oxa-1-thia-dibenzo[e,h]azulene-2-ylmethoxy)-ethyl]-amine hydrochloride,
4-[2-(8-oxa-1-thia-dibenzo[e,h]azulene-2-ylmethoxy)-ethyl]-morpholine hydrochloride,
1-[2-(8-oxa-1-thia-dibenzo[e,h]azulene-2-ylmethoxy)-ethyl]-piperidine hydrochloride,
1-[2-(8-oxa-1-thia-dibenzo[e,h]azulene-2-ylmethoxy)-ethyl]-pyrrolidine hydrochloride,
[3-(9-chloro-8-oxa-1-thia-dibenzo[e,h]azulene-2-ylmethoxy)-propyl]-dimethyl-amine,
[2-(9-chloro-8-oxa-1-thia-dibenzo[e,h]azulene-2-ylmethoxy)-ethyl]-dimethyl-amine,
4-[2-(9-chloro-8-oxa-1-thia-dibenzo[e,h]azulene-2-ylmethoxy)-ethyl]-morpholine,
1-[2-(9-chloro-8-oxa-1-thia-dibenzo[e,h]azulene-2-ylmethoxy)-ethyl]-piperidine,
1-[2-(9-chloro-8-oxa-1-thia-dibenzo[e,h]azulene-2-ylmethoxy)-ethyl]-pyrrolidine,
[3-(11-chloro-8-oxa-1-thia-dibenzo[e,h]azulene-2-ylmethoxy)-propyl]-dimethyl-amine,
[2-(11-chloro-8-oxa-1-thia-dibenzo[e,h]azulene-2-ylmethoxy)-ethyl]-dimethyl-amine,
4-[2-(11-chloro-8-oxa-1-thia-dibenzo[e,h]azulene-2-ylmethoxy)-ethyl]-morpholine,
1-[2-(11-chloro-8-oxa-1-thia-dibenzo[e,h]azulene-2-ylmethoxy)-ethyl]-piperidine,
1-[2-(11-chloro-8-oxa-1-thia-dibenzo[e,h]azulene-2-ylmethoxy)-ethyl]-pyrrolidine,
[3-(11-fluoro-8-oxa-1-thia-dibenzo[e,h]azulene-2-ylmethoxy)-propyl]-dimethyl-amine hydrochloride,
[2-(11-fluoro-8-oxa-1-thia-dibenzo[e,h]azulene-2-ylmethoxy)-ethyl]-dimethyl-amine hydrochloride,
4-[2-(11-fluoro-8-oxa-1-thia-dibenzo[e,h]azulene-2-ylmethoxy)-ethyl]-morpholine hydrochloride,
1-(2-(11-fluoro-8-oxa-1-thia-dibenzo[e,h]azulene-2-ylmethoxy)-ethyl]-piperidine hydrochloride,
1-[2-(11-fluoro-8-oxa-1-thia-dibenzo[e,h]azulene-2-ylmethoxy)-ethyl]-pyrrolidine hydrochloride,
[3-(1,8-dithia-dibenzo[e,h]azulene-2-ylmethoxy)-propyl]-dimethyl-amine hydrochloride,
[2-(1,8-dithia-dibenzo[e,h]azulene-2-ylmethoxy)-ethyl]-dimethyl-amine hydrochloride,
4-[2-(1,8-dithia-dibenzo[e,h]azulene-2-ylmethoxy)-ethyl]-morpholine hydrochloride,
1-[2-(1,8-dithia-dibenzo[e,h]azulene-2-ylmethoxy)-ethyl]-piperidine hydrochloride,
1-[2-(1,8-dithia-dibenzo[e,h]azulene-2-ylmethoxy)-ethyl]-pyrrolidine hydrochloride,
[3-(11-fluoro-1,8-dithia-dibenzo[e,h]azulene-2-ylmethoxy)-propyl]-dimethyl-amine hydrochloride,
[2-(11-fluoro-1,8-dithia-dibenzo[e,h]azulene-2-ylmethoxy)-ethyl]-dimethyl-amine hydrochloride,
4-[2-(11-fluoro-1,8-dithia-dibenzo[e,h]azulene-2-ylmethoxy)-ethyl]-morpholine hydrochloride,
1-[2-(11-fluoro-1,8-dithia-dibenzo[e,h]azulene-2-ylmethoxy)-ethyl]-piperidine hydrochloride,
1-[2-(11-fluoro-1,8-dithia-dibenzo[e,h]azulene-2-ylmethoxy)-ethyl]-pyrrolidine hydrochloride,
[3-(11-chloro-1,8-dithia-dibenzo[e,h]azulene-2-ylmethoxy)-propyl]-dimethyl-amine hydrochloride,
[2-(11-chloro-1,8-dithia-dibenzo[e,h]azulene-2-ylmethoxy)-ethyl]-dimethyl-amine hydrochloride, 4-[2-(11-chloro-1,8-dithia-dibenzo[e,h]azulene-2-ylmethoxy)-ethyl]-morpholine hydrochloride,
1-[2-(11-chloro-1,8-dithia-dibenzo[e,h]azulene-2-ylmethoxy)-ethyl]-piperidine hydrochloride,
1-[2-(11-chloro-1,8-dithia-dibenzo[e,h]azulene-2-ylmethoxy)-ethyl]-pyrrolidine hydrochloride,
[3-(11-bromo-1,8-dithia-dibenzo[e,h]azulene-2-ylmethoxy)-propyl]-dimethyl-amine hydrochloride,
[2-(11-bromo-1,8-dithia-dibenzo[e,h]azulene-2-ylmethoxy)-ethyl]-dimethyl-amine hydrochloride,
4-[2-(11-bromo-1,8-dithia-dibenzo[e,h]azulene-2-ylmethoxy)-ethyl]-morpholine,
1-[2-(11-bromo-1,8-dithia-dibenzo[e,h]azulene-2-ylmethoxy)-ethyl]-piperidine,
1-[2-(11-bromo-1,8-dithia-dibenzo[e,h]azulene-2-ylmethoxy)-ethyl]-pyrrolidine,
[3-(10-trifluoromethyl-1,8-dithia-dibenzo[e,h]azulene-2-ylmethoxy)-propyl]-dimethyl-amine,
dimethyl-[2-(10-trifluoromethyl-1,8-dithia-dibenzo[e,h]azulene-2-ylmethoxy)-ethyl]-amine hydrochloride,
4-[2-(10-trifluoromethyl-1,8-dithia-dibenzo[e,h]azulene-2-ylmethoxy)-ethyl]-morpholine,
1-[2-(10-trifluoromethyl-1,8-dithia-dibenzo[e,h]azulene-2-ylmethoxy)-ethyl]-piperidine hydrochloride,
1-[2-(10-trifluoromethyl-1,8-dithia-dibenzo[e,h]azulene-2-ylmethoxy)-ethyl]-pyrrolidine hydrochloride,
[3-(10-chloro-1,8-dithia-dibenzo[e,h]azulene-2-ylmethoxy)-propyl]-dimethyl-amine,
[2-(10-chloro-1,8-dithia-dibenzo[e,h]azulene-2-ylmethoxy)-ethyl]-dimethyl-amine hydrochloride,
1-[2-(10-chloro-1,8-dithia-dibenzo[e,h]azulene-2-ylmethoxy)-ethyl]-piperidine hydrochloride,
1-[2-(10-chloro-1,8-dithia-dibenzo[e,h]azulene-2-ylmethoxy)-ethyl]-pyrrolidine,
[3-(10-bromo-1,8-dithia-dibenzo[e,h]azulene-2-ylmethoxy)-propyl]-dimethyl-amine hydrochloride,
[2-(10-bromo-1,8-dithia-dibenzo[e,h]azulene-2-ylmethoxy)-ethyl]-dimethyl-amine hydrochloride,
1-[2-(10-bromo-1,8-dithia-dibenzo[e,h]azulene-2-ylmethoxy)-ethyl]-piperidine hydrochloride,
1-[2-(10-bromo-1,8-dithia-dibenzo[e,h]azulene-2-ylmethoxy)-ethyl]-pyrrolidine,
[2-(10-bromo-1,8-dithia-dibenzo[e,h]azulene-2-ylmethoxy)-propyl]-dimethyl-amine hydrochloride,
[3-(9,11-dimethyl-1,8-dithia-dibenzo[e,h]azulene-2-ylmethoxy)-propyl]-dimethyl-amine hydrochloride,
[2-(9,11-dimethyl-1,8-dithia-dibenzo[e,h]azulene-2-ylmethoxy)-ethyl]-dimethyl-amine hydrochloride,
1-[2-(9,11-dimethyl-1,8-dithia-dibenzo[e,h]azulene-2-ylmethoxy)-ethyl]-pyrrolidine hydrochloride,
[3-(10,11-dichloro-1,8-dithia-dibenzo[e,h]azulene-2-ylmethoxy)-propyl]-dimethyl-amine hydrochloride,
[2-(10,11-dichloro-1,8-dithia-dibenzo[e,h]azulene-2-ylmethoxy)-ethyl]-dimethyl-amine hydrochloride,
4-[2-(10,11-dichloro-1,8-dithia-dibenzo[e,h]azulene-2-ylmethoxy)-ethyl]-morpholine hydrochloride,
1-[2-(10,11-dichloro-1,8-dithia-dibenzo[e,h]azulene-2-ylmethoxy)-ethyl]-piperidine hydrochloride,
1-[2-(10,11-dichloro-1,8-dithia-dibenzo[e,h]azulene-2-ylmethoxy)-ethyl]-pyrrolidine hydrochloride,
[3-(9-chloro-11-fluoro-1,8-dithia-dibenzo[e,h]azulene-2-ylmethoxy)-propyl]-dimethyl-amine hydrochloride,
[2-(9-chloro-11-fluoro-1,8-dithia-dibenzo[e,h]azulene-2-ylmethoxy)-ethyl]-dimethyl-amine hydrochloride,
4-(11-fluoro-8-oxa-1-thia-dibenzo[e,h]azulene-2-yl)-but-3-ene-2-one,
4-(11-chloro-8-oxa-1-thia-dibenzo[e,h]azulene-2-yl)-but-3-ene-2-one,
3-(11-fluoro-8-oxa-1-thia-dibenzo[e,h]azulene-2-yl)-acrylic acid,
3-(11-fluoro-8-oxa-1-thia-dibenzo[e,h]azulene-2-yl)-propionic acid,
3-(11-chloro-8-oxa-1-thia-dibenzo[e,h]azulene-2-ylmethoxy)-propylamine,
3-(8-oxa-1-thia-dibenzo[e,h]azulene-2-ylmethoxy)-propylamine,
N,N-dimethyl-[3-(11-methylsulfanyl-1,8-dithia-dibenzo[e,h]azulene-2-ylmethoxy)-propyl]-amine,
N,N-dimethyl-[2-(11-methylsulfanyl-1,8-dithia-dibenzo[e,h]azulene-2-ylmethoxy)-ethyl]-amine,
N,N-dimethyl-[3-(10-methyl-1,8-dithia-dibenzo[e,h]azulene-2-ylmethoxy)-propyl]-amine,
N,N-dimethyl-[2-(10-methyl-1,8dithia-dibenzo[e,h]azulene-2-ylmethoxy)-ethyl]-amine,
N,N-dimethyl-[3-(11-methyl-1,8-dithia-dibenzo[e,h]azulene-2-ylmethoxy)-propyl]-amine,
N,N-dimethyl-[2-(11-methyl-1,8-dithia-dibenzo[e,h]azulene-2-ylmethoxy)-ethyl]-amine,
N,N-dimethyl-[3-(10-methoxy-8-oxa-1-thia-dibenzo[e,h]azulene-2-ylmethoxy)-propyl]-amine,
N,N-dimethyl-[2-(10-methoxy-8-oxa-1-thia-dibenzo[e,h]azulene-2-ylmethoxy)-ethyl]-amine,
1-(2-(10-methoxy-8-oxa-1-thia-dibenzo[e,h]azulene-2-ylmethoxy)-ethyl]-piperidine,
1-(2-(10-methoxy-8-oxa-1-thia-dibenzo[e,h]azulene-2-ylmethoxy)-ethyl]-pyrrolidine,
3-(10-methoxy-8-oxa-1-thia-dibenzo[e,h]azulene-2-ylmethoxy)-propylamine,
N,N-dimethyl-[3-(6-chloro-1,8-dithia-dibenzo[e,h]azulene-2-ylmethoxy)-propyl-amine,
N,N-dimethyl-[2-(6-chloro-1,8-dithia-dibenzo[e,h]azulene-2-ylmethoxy)-ethyl]-amine,
3-(6-chloro-1,8-dithia-dibenzo[e,h]azulene-2-ylmethoxy)-propyl]-amine,
N,N-dimethyl-[3-(10-fluoro-1,8-dithia-dibenzo[e,h]azulene-2-ylmethoxy)-propyl]-amine,
N,N-dimethyl-[2-(10-fluoro-1,8-dithia-dibenzo[e,h]azulene-2-ylmethoxy)-ethyl]-amine,
[2-(3-dimethylamino-propoxymethyl)-1-thia-8-aza-dibenzo[e,h]azulene-8-yl)-phenyl-methanon,
[2-(2-dimethylamino-ethoxymethyl)-1-thia-8-aza-dibenzo[e,h]azulene-8-yl)-phenyl-methanon,
N,N-dimethyl-[3-(8H-1-thia-8-aza-dibenzo[e,h]azulene-2-ylmethoxy)-propyl]-amine,
N,N-dimethyl-[2-(8H-1-thia-8-aza-dibenzo[e,h]azulene-2-ylmethoxy)-ethyl]-amine,
[3-(11-fluoro-8-oxa-1-thia-dibenzo[e,h]azulene-2-ylmethoxy)-propylamine hydrochloride,
[3-(1,8-dithia-dibenzo[e,h]azulene-2-ylmethoxy]-propylamine,
N,N-dimethyl-{3-[3-(8-oxa-1-thia-dibenzo[e,h]azulene-2-yl)-propyloxy]-propyl}-amine,
N,N-dimethyl-{2-[3-(8-oxa-1-thia-dibenzo[e,h]azulene-2-yl)-propyloxy]-ethyl}-amine, N,N-dimethyl-{3-[3-(1,8-dithia-dibenzo[e,h]azulene-2-yl)-propyloxy]-propyl}-amine,
N,N-dimethyl-{2-[3-(1,8-dithia-dibenzo[e,h]azulene-2-yl)-propyloxy]-ethyl}-amine,
N,N-dimethyl-{3-(8H-1-thia-dibenzo[e,h]azulene-2-yl)-methoxy]-propyl}-amine,
N,N-dimethyl-{2-(8H-1-thia-dibenzo[e,h]azulene-2-yl)-methoxy]-ethyl}-amine,
N,N-dimethyl-{3-[3-(1,8-dithia-dibenzo[e,h]azulene-2-yl)-allyloxy]-propyl}-amine,
N,N-dimethyl-{2-[3-(1,8-dithia-dibenzo[e,h]azulene-2-yl)-allyloxy]-ethyl}-amine,
N-methyl-[3-(11-chloro-8-oxa-1-thia-dibenzo[e,h]azulene-2-ylmethoxy)-propyl]-amine,
N-methyl-[2-(11-chloro-8-oxa-1-thia-dibenzo[e,h]azulene-2-ylmethoxy)-ethyl]-amine,
N-methyl-[3-(8-oxa-1-thia-dibenzo[e,h]azulene-2-ylmethoxy)-propyl]-amine,
N-methyl-[3-(1,8-dithia-dibenzo[e,h]azulene-2-ylmethoxy)-propyl]-amine,
2-bromomethyl-1,8-dithia-dibenzo[e,h]azulene, and
2-(1,8-dithia-dibenzo[e,h]azulene-2-yl)-ethylamine, and salts and hydrates thereof.

30. The method of claim 16 wherein the compound or formula I is [2-(11-chloro-8-oxa-1-thia-dibenzo[e,h]azulene-2-ylmethoxy)-ethyl]-dimethyl-amine.

31. A pharmaceutical composition comprising a compound as claimed in claim 1 or a pharmaceutically acceptable salt or hydrate thereof and a pharmaceutically acceptable diluent or carrier.

32. The pharmaceutical composition according to claim 31 wherein $R_{10}$ represents $CH_2OH$, $CH=CHCH_2OH$ or $CH_2CH_2CH_2OH$.

33. The pharmaceutical composition according to claim 31 wherein $R_{10}$ represents $(CH_2)_nA$, $CH_2O(CH_2)_n$-A, $CH=CHCH_2O(CH_2)_n$-A or $CH_2CH_2CH_2O(CH_2)_n$-A.

34. The pharmaceutical composition according to claim 31 wherein A represents morpholine-4-yl, piperidine-1-yl or pyrrolidine-1-yl.

35. The pharmaceutical composition according to claim 31 wherein A represents

wherein $R_{11}$ and $R_{12}$ are as defined in claim 1.

36. The pharmaceutical composition according to claim 31 wherein $R_{11}$ and $R_{12}$ represent H, —$CH_3$ or —$CH_2CH_3$.

37. The pharmaceutical composition according to claim 31 wherein $R_2$ represents H, $SCH_3$, F, Cl, Br or $CH_3$.

38. The pharmaceutical composition according to claim 31 wherein $R_3$ represents H, $OCH_3$, F, Cl, Br, $CF_3$ or $CH_3$.

39. The pharmaceutical composition according to claim wherein $R_4$ reprsents H, F, Cl or $CH_3$.

40. The pharmaceutical composition according to claim 31 wherein $R_6$ represents H, F or Cl.

41. The pharmaceutical composition according to claim 31 wherein $R_{10}$ represents $C_1$–$C_{15}$ hydroxyalkyl or $C_1$–$C_{15}$ alkylamino represented by the formula $(CH_2)_n$-A.

42. The pharmaceutical composition according to claim 41 wherein said heteroaryl group is selected from the group consisting of thiophene, pyrrole, imidazole, pyridine, oxazole, thiazole, pyrazole, tetrazole, pyrimidine, pyrazine and triazine.

43. The pharmaceutical composition according to claim 31 wherein said heteroaryl group is selected from the group consisting of thiophene, pyrrole, imidazole, pyridine, oxazole, thiazole, pyrazole, tetrazole, pyrimidine, pyrazine triazine.

44. The pharmaceutical composition according to claim 31 wherein the compound according to claim 1 is selected from the group consisting of:
dimethyl-[3-(8-oxa-1-thia-dibenzo[e,h]azulene-2-ylmethoxy)-propyl]-amine hydrochloride,
dimethyl-[2-(8-oxa-1-thia-dibenzo[e,h]azulene-2-ylmethoxy)-ethyl]-amine hydrochloride,
4-[2-(8-oxa-1-thia-dibenzo[e,h]azulene-2-ylmethoxy)-ethyl]-morpholine hydrochloride,
1-[2-(8-oxa-1-thia-dibenzo[e,h]azulene-2-ylmethoxy)-ethyl]-piperidine hydrochloride,
1-[2-(8-oxa-1-thia-dibenzo[e,h]azulene-2-ylmethoxy)-ethyl]-pyrrolidine hydrochloride,
[3-(9-chloro-8-oxa-1-thia-dibenzo[e,h]azulene-2-ylmethoxy)-propyl]-dimethyl-amine,
[2-(9-chloro-8-oxa-1-thia-dibenzo[e,h]azulene-2-ylmethoxy)-ethyl]-dimethyl-amine,
4-[2-(9-chloro-8-oxa-1-thia-dibenzo[e,h]azulene-2-ylmethoxy)-ethyl]-morpholine,
1-[2-(9-chloro-8-oxa-1-thia-dibenzo[e,h]azulene-2-ylmethoxy)-ethyl]-piperidine,
1-[2-(9-chloro-8-oxa-1-thia-dibenzo[e,h]azulene-2-ylmethoxy)-ethyl]-pyrrolidine,
[3-(11-chloro-8-oxa-1-thia-dibenzo[e,h]azulene-2-ylmethoxy)-propyl]-dimethyl-amine,
[2-(11-chloro-8-oxa-1-thia-dibenzo[e,h]azulene-2-ylmethoxy)-ethyl]-dimethyl-amine,
4-[2-(11-chloro-8-oxa-1-thia-dibenzo[e,h]azulene-2-ylmethoxy)-ethyl]-morpholine,
1-[2-(11-chloro-8-oxa-1-thia-dibenzo[e,h]azulene-2-ylmethoxy)-ethyl]-piperidine,
1-[2-(11-chloro-8-oxa-1-thia-dibenzo[e,h]azulene-2-ylmethoxy)-ethyl]-pyrrolidine,
[3-(11-fluoro-8-oxa-1-thia-dibenzo[e,h]azulene-2-ylmethoxy)-propyl]-dimethyl-amine hydrochloride,
[2-(11-fluoro-8-oxa-1-thia-dibenzo[e,h]azulene-2-ylmethoxy)-ethyl]-dimethyl-amine hydrochloride,
4-[2-(11-fluoro-8-oxa-1-thia-dibenzo[e,h]azulene-2-ylmethoxy)-ethyl]-morpholine hydrochloride,
1-[2-(11-fluoro-8-oxa-1-thia-dibenzo[e,h]azulene-2-ylmethoxy)-ethyl]-piperidine hydrochloride,
1-[2-(11-fluoro-8-oxa-1-thia-dibenzo[e,h]azulene-2-ylmethoxy)-ethyl]-pyrrolidine hydrochloride,
[3-(1,8-dithia-dibenzo[e,h]azulene-2-ylmethoxy)-propyl]-dimethyl-amine hydrochloride,
[2-(1,8-dithia-dibenzo[e,h]azulene-2-ylmethoxy)-ethyl]-dimethyl-amine hydrochloride,
4-[2-(1,8-dithia-dibenzo[e,h]azulene-2-ylmethoxy)-ethyl]-morpholine hydrochloride,
1-[2-(1,8-dithia-dibenzo[e,h]azulene-2-ylmethoxy)-ethyl]-piperidine hydrochloride,
1-[2-(1,8-dithia-dibenzo[e,h]azulene-2-ylmethoxy)-ethyl]-pyrrolidine hydrochloride,
[3-(11-fluoro-1,8-dithia-dibenzo[e,h]azulene-2-ylmethoxy)-propyl]-dimethyl-amine hydrochloride,
[2-(11-fluoro-1,8-dithia-dibenzo[e,h]azulene-2-ylmethoxy)-ethyl]-dimethyl-amine hydrochloride, 4-[2-(11-fluoro-1,8-dithia-dibenzo[e,h]azulene-2-ylmethoxy)-ethyl]-morpholine hydrochloride,
1-[2-(11-fluoro-1,8-dithia-dibenzo[e,h]azulene-2-ylmethoxy)-ethyl]-piperidine hydrochloride,
1-[2-(11-fluoro-1,8-dithia-dibenzo[e,h]azulene-2-ylmethoxy)-ethyl]-pyrrolidine hydrochloride,
[3-(11-chloro-1,8-dithia-dibenzo[e,h]azulene-2-ylmethoxy)-propyl]-dimethyl-amine hydrochloride,
[2-(11-chloro-1,8-dithia-dibenzo[e,h]azulene-2-ylmethoxy)-ethyl]-dimethyl-amine hydrochloride,
4-[2-(11-chloro-1,8-dithia-dibenzo[e,h]azulene-2-ylmethoxy)-ethyl]-morpholine hydrochloride,
1-[2-(11-chloro-1,8-dithia-dibenzo[e,h]azulene-2-ylmethoxy)-ethyl]-piperidine hydrochloride,
1-[2-(11-chloro-1,8-dithia-dibenzo[e,h]azulene-2-ylmethoxy)-ethyl]-pyrrolidine hydrochloride,
[3-(11-bromo-1,8-dithia-dibenzo[e,h]azulene-2-ylmethoxy)-propyl]-dimethyl-amine hydrochloride,
[2-(11-bromo-1,8-dithia-dibenzo[e,h]azulene-2-ylmethoxy)-ethyl]-dimethyl-amine hydrochloride,
4-[2-(11-bromo-1,8-dithia-dibenzo[e,h]azulene-2-ylmethoxy)-ethyl]-morpholine,
1-[2-(11-bromo-1,8-dithia-dibenzo[e,h]azulene-2-ylmethoxy)-ethyl]-piperidine,
1-[2-(11-bromo-1,8-dithia-dibenzo[e,h]azulene-2-ylmethoxy)-ethyl]-pyrrolidine,
[3-(10-trifluoromethyl-1,8-dithia-dibenzo[e,h]azulene-2-ylmethoxy)propyl]-dimethyl-amine,
dimethyl-[2-(10-trifluoromethyl-1,8-dithia-dibenzo[e,h]azulene-2-ylmethoxy)-ethyl]-amine hydrochloride,
4-[2-(10-trifluoromethyl-1,8-dithia-dibenzo[e,h]azulene-2-ylmethoxy)-ethyl]-morpholine,
1-[2-(10-trifluoromethyl-1,8-dithia-dibenzo[e,h]azulene-2-ylmethoxy)-ethyl]-piperidine hydrochloride,
1-[2-(10-trifluoromethyl-1,8-dithia-dibenzo[e,h]azulene-2-ylmethoxy)-ethyl]-pyrrolidine hydrochloride,
[3-(10-chloro-1,8-dithia-dibenzo[e,h]azulene-2-ylmethoxy)-propyl]-dimethyl-amine,
[2-(10-chloro-1,8-dithia-dibenzo[e,h]azulene-2-ylmethoxy)-ethyl]-dimethyl-amine hydrochloride,
1-[2-(10-chloro-1,8-dithia-dibenzo[e,h]azulene-2-ylmethoxy)-ethyl]-piperidine hydrochloride,
1-[2-(10-chloro-1,8-dithia-dibenzo[e,h]azulene-2-ylmethoxy)-ethyl]-pyrrolidine,
[3-(10-bromo-1,8-dithia-dibenzo[e,h]azulene-2-ylmethoxy)-propyl]-dimethyl-amine hydrochloride,
[2-(10-bromo-1,8-dithia-dibenzo[e,h]azulene-2-ylmethoxy)-ethyl]-dimethyl-amine hydrochloride,
1-[2-(10-bromo-1,8-dithia-dibenzo[e,h]azulene-2-ylmethoxy)-ethyl]-piperidine,
1-[2-(10-bromo-1,8-dithia-dibenzo[e,h]azulene-2-ylmethoxy)-ethyl]-pyrrolidine,
[2-(10-bromo-1,8-dithia-dibenzo[e,h]azulene-2-ylmethoxy)-propyl]-dimethyl-amine hydrochloride,
[3-(9, 11-dimethyl-1,8-dithia-dibenzo[e,h]azulene-2-ylmethoxy)-propyl]-dimethyl-amine hydrochloride,
[2-(9,11-dimethyl-1,8-dithia-dibenzo[e,h]azulene-2-ylmethoxy)-ethyl]-dimethyl-amine hydrochloride,
1-[2-(9,11-dimethyl-1,8-dithia-dibenzo[e,h]azulene-2-ylmethoxy)-ethyl]-pyrrolidine hydrochloride,
[3-(10,11-dichloro-1,8-dithia-dibenzo[e,h]azulene-2-ylmethoxy)-propyl]-dimethyl-amine hydrochloride,
[2-(10,11-dichloro-1,8-dithia-dibenzo[e,h]azulene-2-ylmethoxy)-ethyl]-dimethyl-amine hydrochloride,
4-[2-(10,11-dichloro-1,8-dithia-dibenzo[e,h]azulene-2-ylmethoxy)-ethyl]-morpholine hydrochloride,
1-[2-(10,11-dichloro-1,8-dithia-dibenzo[e,h]azulene-2-ylmethoxy)-ethyl]-piperidine hydrochloride,
1-[2-(10,11-dichloro-1,8-dithia-dibenzo[e,h]azulene-2-ylmethoxy)-ethyl]-pyrrolidine hydrochloride,
[3-(9-chloro-11-fluoro-1,8-dithia-dibenzo[e,h]azulene-2-ylmethoxy)-propyl]-dimethyl-amine hydrochloride,
[2-(9-chloro-11-fluoro-1,8-dithia-dibenzo[e,h]azulene-2-ylmethoxy)-ethyl]-dimethyl-amine hydrochloride,
4-(11-fluoro-8-oxa-1-thia-dibenzo[e,h]azulene-2-yl)-but-3-ene-2-one,
4-(11-chloro-8-oxa-1-thia-dibenzo[e,h]azulene-2-yl)-but-3-ene-2-one,
3-(11-fluoro-8-oxa-1-thia-dibenzo[e,h]azulene-2-yl)-acrylic acid,
3-(11-fluoro-8-oxa-1-thia-dibenzo[e,h]azulene-2-yl)-propionic acid,
3-(11-chloro-8-oxa-1-thia-dibenzo[e,h]azulene-2-ylmethoxy)-propylamine,
3-(8-oxa-1-thia-dibenzo[e,h]azulene-2-ylmethoxy)-propylamine,
N,N-dimethyl-[3-(11-methylsulfanyl-1,8-dithia-dibenzo[e,h]azulene-2-ylmethoxy)-propyl]-amine,
N,N-dimethyl-[2-(11-methylsulfanyl-1,8-dithia-dibenzo[e,h]azulene-2-ylmethoxy)-ethyl]-amine,
N,N-dimethyl-[3-(10-methyl-1,8-dithia-dibenzo[e,h]azulene-2-ylmethoxy)-propyl]-amine,
N,N-dimethyl-[2-(10-methyl-1,8-dithia-dibenzo[e,h]azulene-2-ylmethoxy)-ethyl]-amine,
N,N-dimethyl-[3-(11-methyl-1,8-dithia-dibenzo[e,h]azulene-2-ylmethoxy)-propyl]-amine,
N,N-dimethyl-[2-(11-methyl-1,8-dithia-dibenzo[e,h]azulene-2-ylmethoxy)-ethyl]-amine,
N,N-dimethyl-[3-(10-methoxy-8-oxa-1-thia-dibenzo[e,h]azulene-2-ylmethoxy)-propyl]-amine,
N,N-dimethyl-[2-(10-methoxy-8-oxa-1-thia-dibenzo[e,h]azulene-2-ylmethoxy)-ethyl]-amine,
1-(2-(10-methoxy-8-oxa-1-thia-dibenzo[e,h]azulene-2-ylmethoxy)-ethyl]-piperidine,
1-(2-(10-methoxy-8-oxa-1-thia-dibenzo[e,h]azulene-2-ylmethoxy)-ethyl]-pyrrolidine,
3-(10-methoxy-8-oxa-1-thia-dibenzo[e,h]azulene-2-ylmethoxy)-propylamine,
N,N-dimethyl-[3-(6-chloro-1,8-dithia-dibenzo[e,h]azulene-2-ylmethoxy)-propyl]-amine,
N,N-dimethyl-[2-(6-chloro-1,8-dithia-dibenzo[e,h]azulene-2-ylmethoxy)-ethyl]-amine,
3-(6-chloro-1,8-dithia-dibenzo[e,h]azulene-2-ylmethoxy)-propyl]-amine,
N,N-dimethyl-[3-(10-fluoro-1,8-dithia-dibenzo[e,h]azulene-2-ylmethoxy)-propyl]-amine,
N,N-dimethyl-[2-(10-fluoro-1,8-dithia-dibenzo[e,h]azulene-2-ylmethoxy)-ethyl]amine,
[2-(3-dimethylamino-propoxymethyl)-1-thia-8-aza-dibenzo[e,h]azulene-8-yl)-phenyl-methanon,
[2-(2-dimethylamino-ethoxymethyl)-1-thia-8-aza-dibenzo[e,h]azulene-8-yl)-phenyl-methanon,
N,N-dimethyl-[3-(8H-1-thia-8-aza-dibenzo[e,h]azulene-2-ylmethoxy)-propyl]-amine, N,N-dimethyl-[2-(8H-1-thia-8-aza-dibenzo[e,h]azulene-2-ylmethoxy)-ethyl]-amine,

[3-(11-fluoro-8-oxa-1-thia-dibenzo[e,h]azulene-2-ylmethoxy)-propylamine hydrochloride,

[3-(1,8-dithia-dibenzo[e,h]azulene-2-ylmethoxy]-propylamine,

N,N-dimethyl-{3-[3-(8-oxa-1-thia-dibenzo[e,h]azulene-2-yl)-propyloxy]-propyl}-amine, N,N-dimethyl-{2-[3-(8-oxa-1-thia-dibenzo[e,h]azulene-2-yl)-propyloxy]-ethyl}-amine, N,N-dimethyl-{3-[3-(1,8-dithia-dibenzo[e,h]azulene-2-yl)-propyloxy]-propyl}amine, N,N-dimethyl-{2-[3-(1,8-dithia-dibenzo[e,h]azulene-2-yl)-propyloxy]-ethyl}-amine, N,N-dimethyl-{3-(8H-1-thia-dibenzo[e,h]azulene-2-yl)-methoxy]-propyl}-amine, N,N-dimethyl-{2-(8H-1-thia-dibenzo[e,h]azulene-2-yl)-methoxyl-ethyl}-amine, N,N-dimethyl-{3-[3-(1,8-dithia-dibenzo[e,h]azulene-2-yl)-allyloxy]-propyl}-amine, N,N-dimethyl-{2-[3-(1,8-dithia-dibenzo[e,h]azulene-2-yl)-allyloxy]-ethyl}-amine, N-methyl-[3-(11-chloro-8-oxa-1-thia-dibenzo[e,h]azulene-2-ylmethoxy)-propyl]-amine, N-methyl-[2-(11-chloro-8-oxa-1-thia-dibenzo[e,h]azulene-2-ylmethoxy)-ethyl]-amine, N-methyl-[3-(8-oxa-1-thia-dibenzo[e,h]azulene-2-ylmethoxy)-propyl]-amine, N-methyl-[3-(1,8-dithia-dibenzo[e,h]azulene-2-ylmethoxy)-propyl]-amine, 2-bromomethyl-1,8-dithia-dibenzo[e,h]azulene, and 2-(1,8-dithia-dibenzo[e,h]azulene-2-yl)-ethylamine, and salts and hydrates thereof.

45. The pharmaceutical composition according to claim 31 wherein the compound of Formula I is [2-(11-chloro-8-oxa-1-thia-dibenzo[e,h]azulene-2-ylmethoxy)-ethyl]-dimethyl-amine.

\* \* \* \* \*